United States Patent
Betlach et al.

(10) Patent No.: US 6,262,340 B1
(45) Date of Patent: Jul. 17, 2001

(54) PRODUCTION OF POLYKETIDES IN PLANTS

(75) Inventors: Mary C. Betlach, San Francisco; James T. Kealey, Davis; Neal Gutterson, Oakland; Ed Ralston, Pleasant Hill, all of CA (US)

(73) Assignee: Kosan Biosciences, Inc., Burlingame, CA (US)

( * ) Notice: Subject to any disclaimer, the term of this patent is extended or adjusted under 35 U.S.C. 154(b) by 0 days.

(21) Appl. No.: 09/114,083

(22) Filed: Jul. 10, 1998

Related U.S. Application Data

(60) Provisional application No. 60/052,211, filed on Jul. 10, 1997.

(51) Int. Cl.$^7$ .............................. A01H 1/00; C12N 15/82; C12N 15/87; C12N 5/00; C12N 5/04

(52) U.S. Cl. .................... 800/278; 435/410; 435/69.1; 435/411; 435/419; 800/281; 800/284

(58) Field of Search .................... 435/410, 69.1, 435/411, 419; 800/278, 281, 284

(56) References Cited

U.S. PATENT DOCUMENTS

| | | | |
|---|---|---|---|
| 5,098,837 | 3/1992 | Beckmann et al. | 435/6 |
| 5,252,474 | 10/1993 | Gewain et al. | 435/91.1 |
| 5,283,173 | 2/1994 | Fields | 435/6 |
| 5,672,491 | 9/1997 | Khosla et al. | 435/148 |
| 5,698,425 | 12/1997 | Ligon et al. | 800/279 |
| 5,712,146 | 1/1998 | Khosla et al. | 435/252.35 |
| 5,716,849 | 2/1998 | Ligon et al. | 435/419 |
| 5,717,084 | 2/1998 | Herrara-Estrella et al. | 536/23.4 |
| 5,728,925 | 3/1998 | Herrara-Estrella et al. | 800/300 |
| 5,830,750 | 11/1998 | Khosla et al. | 435/252.35 |
| 5,843,718 | 11/1998 | Khosla et al. | 435/69.1 |

FOREIGN PATENT DOCUMENTS

| | | |
|---|---|---|
| 0 791 655 | 8/1997 | (EP) . |
| WO 95/08548 | 3/1995 | (WO) . |
| WO 95/08633 | 3/1995 | (WO) . |
| WO 95/33818 | 12/1995 | (WO) . |
| WO 96/40968 | 12/1996 | (WO) . |
| WO 97/13845 | 4/1997 | (WO) . |
| WO 98/01571 | 1/1998 | (WO) . |
| WO 98/10546 | 3/1998 | (WO) . |
| WO 98/27203 | 6/1998 | (WO) . |
| WO 98/55625 | 12/1998 | (WO) . |

OTHER PUBLICATIONS

Boase et al. In Vitrol Cellular and Developmental Biology. 1998. vol. 34: 46–51.*

Bartel, R.L., et al., "Biosynthesis of anthraquinones by interspecies cloning of actinorhodin biosynthesis genes in streptomycetes: clarification of actinorhodin gene functions," *J Bacteriol* (1990), 172(9):4816–4826.

Bechtold, N., et al., "In planta agrobacterium mediated gene transfer by infiltration of adult *arabidopsis thaliana* plants," *C.R. Acad. Sci. Paris/Life Sciences* (1993), 316:1194–1199.

Bevan, M., "Binary agrobacterium vectors for plant transformation," *Nucleic Acids Research* (1984), 12:8711–8721.

Bibb, M.J., et al., "Analysis of the nucleotide sequence of the *streptomyces glaucescens* tcmI genes provides key information about the enzymology of polyketide antibiotic biosynthesis," *EMBO J* (1989), 8(9):2727–2736.

Borchert, S., et al., "Induction of surfactin production in *bacillus subtilis* by gsp, a gene located upstream of the gramicidin S operon in *bacillus brevis*," *J. Bacteriol* (1994), 176:2458–2462.

Bramwell, H., et al., "Propionyl–coA carboxylase from *streptomyces coelicolor* A3(2): cloning of the gene encoding the biotin–containing subunit," *Microbiology* (1996), 142(3):649–655.

Broach, J.R., et al., "High–throughput screening for drug discovery" *Nature* (1996) 384(Supp.):14–16.

Carreras, C.W., et al., "Utilization of enzymatically phosphopantetheinylated acyl carrier proteins and acetyl–acyl carrier proteins by the actinorhodin polyketide synthase," *Biochemistry* (1997), 36:11757–11761.

Chang, A.C.Y., et al., "Construction and characterization of amplifiable multicopy DNA cloning vehicles derived from the P15A cryptic miniplasmid," *J Bacteriol* (1978), 134:1141–1156.

Chater, K.F., et al., "Resistance, regulatory and production genes for the antibiotic methylenomycin are clustered," *EMBO J* (1985), 4:1893–1897.

Cortes, J., et al., "An unusually large multifunctional polypeptide in the erythromycin–producing polyketide synthase of *saccharopolyspora erythraea*," *Nature* (1990), 348:176–178.

Cox, R.J., et al., "Post–translational modification of heterologously expressed streptomyces type II polyketide synthase acyl carrier proteins," *FEBS Letters* (1997), 405:267–272.

Crossway, A., et al., "Integration of foreign DNA following microinjection of tobacco mesophyll protoplasts," *Mol Gen Genet* (1986), 202:179–185.

Dalbadie–McFarland, G., et al., "Oligonucleotide–directed mutagenesis as a general and powerful method for studies of protein function," *Proc Natl Acad Sci USA* (1982), 79:6409–6413.

(List continued on next page.)

Primary Examiner—Paula K. Hutzell
Assistant Examiner—Ousama Zaghmout
(74) *Attorney, Agent, or Firm*—Morrison & Foerster; Kevin Kaster; Kate Murasurge

(57) ABSTRACT

The present invention provides genetically altered plants and plant cells that have been modified to contain expression system(s) capable of expressing a functional polyketide synthase (PKS). The present invention further provides methods of producing PKS and polyketides using these plants and cells.

65 Claims, 3 Drawing Sheets

OTHER PUBLICATIONS

De Block, M., et al., "Expression of foreign genes in regenerated plants and in their progeny," *EMBO J* (1984), 3:1681–1689.

De Greve, H., et al., "Nucleotide sequence and transcript map of the *agrobacterium tumefaciens* Ti plasmid–encoded octopine synthase gene," *J Mol Appl Genet* (1983), 1:499–511.

de la Peña, A., et al., "Transgenic rye plants obtained by injecting DNA into young floral tillers," *Nature* (1987), 325:274–276.

Depicker, A., et al., "Nopaline synthase: transcript mapping and DNA sequence," *J Mol Appl Genet* (1982), 1:561–573.

Donadio, S., et al., "Modular organization of genes required for complex polyketide biosynthesis," *Science* (1991), 252:675–679.

Edge, M.D., et al., "Total synthesis of a human leukocyte interferon gene," *Nature* (1981), 292:756–762.

Fernández–Moreno, M.A., et al., "Nucleotide sequence and deduced functions of a set of cotranscribed genes of *streptomyces coelicolor* A3(2) including a polyketide synthase for the antibiotic actinorhodin," *J Biol Chem* (1992), 267:19278–19290.

Fraley, R.T., et al., "Liposome–mediated delivery of tobacco mosaic virus RNA into tobacco protoplasts: a sensitive assay for monitoring liposome–protoplast interactions," *Proc Natl Acad Sci USA* (1982), 79:1859–1863.

Fraley, R.T., et al., "Expression of bacterial genes in plant cells," *Proc Natl Acad Sci USA* (1983), 80:4803–4807.

Fromm, M., et al., "Expression of genes transferred into monocot and dicot plant cells by electroporation," *Proc Natl Acad Sci USA* (1985), 82:5824–5828.

Fujii, I., et al., "Cloning of the polyketide synthase gene atX from *Aspergillus terreus* and its identification as the 6–MethyIsalicylic acid synthase gene by heterologous expression," *Mol Gen Genet* (1996), 253:1–10.

Gehring, A.M., et al., "Enterobactin biosynthesis in *escherichia coli*: isochorismate lyase (EntB) is a bifunctional enzyme that is phosphopantetheinylated by EntD and then acylated by EntE using ATP and 2,3–dihydroxybenzoate," *Biochem* (1997), 36:8495–8503.

Geisselsoder, J., et al., "Efficient site–directed in vitro mutagenesis," *BioTechniques* (1987), 5:786–791.

Gielen, J., et al., "The complete nucleotide sequence of the TL–DNA of the *agrobacterium tumefaciens* plasmid pTi-Ach5," *EMBO J* (1984), 3:835–846.

Gietl, C., "Protein targeting and import into plant peroxisomes," *Physiologia Plantarum* (1996), 97:599–608.

Hoekema, A., et al., "A binary plant vector strategy based on separation of vir– and T–region of the *agrobacterium tumefaciens* Ti–plasmid," *Nature* (1983), 303:179–180.

Hooykas–Van Slogteren, G.M.S., et al., "Expression of Ti plasmid genes in monocotyledonous plants infected with *agrobacterium tumefaciens*," *Nature* (1984), 311:763–764.

Hopwood, D.A., et al., "Production of 'hybrid' antibiotics by genetic engineering," *Nature* (1985), 314:642–644.

Ikeda, H., et al., "Avermectin biosynthesis," *Chem Rev* (1997), 97:2591–2609.

Itoh, Y., et al., "Genetic and molecular characterization of the pseudomonas plasmid p VS1," *Plasmid* (1984), 11:206–220.

Jay, E., et al., "Chemical synthesis of a biologically active gene for human immune interferon–γ," *J Biol Chem* (1984), 259:6311–6317.

Kao, C.M., et al., "Manipulation of macrolide ring size by directed mutagenesis of a modular polyketide synthase," *J Am Chem Soc* (1995), 117:9105–9106.

Kay, R., et al., "Duplication of CaMV 35S promoter sequences creates a strong enhancer for plant genes," *Science* (1987), 236:1299–1302.

Kealey, J.T., et al., "Production of a polyketide natural product in nonpolyketide–producing prokaryotic and eukaryotic hosts," *Proc Natl Acad Sci USA* (1998), 95:505–509.

Khosla, C., et al., "Genetic construction and functional analysis of hybrid polyketide synthases containing heterologous acyl carrier proteins," *J Bacteriol* (1993), 175:2197–2204.

Klein, T.M., et al., "High–velocity microprojectiles for delivering nucleic acids into living cells," *Nature* (1987), 327:70–73.

Komiya, T., et al., "Binding of mitochondrial precursor proteins to the cytoplasmic domains of the import receptors Tom70 and Tom20 is determined by cytoplasmic chaperones," *EMBO J* (1997), 16:4267–4275.

Koncz, C., et al., "The promoter of $T_L$–DNA gene 5 controls the tissue–specific expression of chimaeric genes carried by a novel type of agrobacterium binary vector," *Mol Gen Genet* (1986), 204:383–396.

Krens, F.A., et al., "In vitro transformation of plant protoplasts with Ti–plasmid DNA," *Nature* (1982), 296:72–74.

Kunkel, T.A., "Rapid and efficient site–specific mutagenesis without phenotypic selection," *Proc Natl Acad Sci USA* (1985), 82:488–492.

Lambalot, R.H., et al., "A new enzyme superfamily—the phosphopantetheinyl transferases," *Chem and Biol* (1996), 3:923–936.

Lawton, M.A., et al., "Expression of a soybean β–conclycinin gene under the control of the cauliflower mosaic virus 35S and 19S promoters in transformed petunia tissues," *Plant Mol Biol* (1987), 9:315–324.

Lee, K.Y., et al., "The molecular basis of sulfonylurea herbicide resistance in tobacco," *EMBO J* (1988), 7:1241–1248.

MacNeil, D.J., et al., "Complex organization of the *streptomyces avermitilis* genes encoding the avermectin polyketide synthase," *Gene* (1992), 115:119–125.

Malpartida, F., et al., "Molecular cloning of the whole biosynthetic pathway of a streptomyces antibiotic and its expression in a heterologous host," *Nature* (1984), 309:462–464.

Matouschek, A., et al., "Active unfolding of precursor proteins during mitochondrial protein import," *EMBO J* (1997), 16:6727–6736.

Murashige, T., et al., "A revised medium for rapid growth and bio assays with tobacco tissue cultures," *Physiologia Planatarum* (1962), 15:473–497.

Nambair, K.P., et al., "Total synthesis and cloning of a gene coding for the ribonuclease S protein," *Science* (1984), 223:1299–1301.

Nawrath, C., et al., "Targeting of the polyhydroxybutyrate biosynthetic pathway to the plastids of *arabidopsis thaliana* results in high levels of polymer accumulation," *Proc Natl Acad Sci USA* (1994), 91:12760–12764.

Olsen, L.J., et al., "Peroxisomes and their assembly in higher plants," *Ann Rev Plant Physiol Plant Mol Biol* (1995), 46:123–146.

Rhodes, C.A., et al., "Genetically transformed maize plants from prototypes," *Science* (1988), 240:204–207.

Roberts, G.A., et al., "Heterologous expression in *escherichia coli* of an intact multienzyme component of the erythromycin–producing polyketide synthase," *Eur J Biochem* (1993), 214:305–311.

Ruvkum, G.B., et al., "A general method for site–directed mutagenesis in prokaryotes," *Nature* (1981), 289:85–88.

St. Schell, J., "Transgenic plants as tools to study the molecular organization of plant genes," *Science* (1987), 237:1176–1183.

Schröder, J., et al., "Plant polyketide synthases: a chalcone synthase–type enzyme with performs a condensation reaction with methylmalonyl–CoA in the biosynthesis of C–methylated chalcones," *Biochemistry* (1998), 37:8417–8425.

Sherman, D.H., et al., "Structure and deduced function of the granaticin–producing polyketide synthase gene cluster of *streptomyces violaceoruber* Tü22," *EMBO J* (1989), 8:2717–2725.

Sherman, D.H., et al., "Functional replacement of genes for individual polyketide synthase components in *streptomyces coelicolor* A3(2) by heterologous genes from a different polyketide pathway," *J Bacteriol* (1992), 174:6184–6190.

Shimamoto, K., et al., "Fertile transgenic rice plants regenerated from transformed protoplasts," *Nature* (1989), 338:274–276.

van den Elzen, P., et al., "Simple binary vectors for DNA transfer to plant cells," *Plant Mol Biol* (1985), 5:149–154.

Waters, S.H., et al., "The tetracycline resistance determinants of RP1 and Tn1721: nucleotide sequence analysis," *Nucleic Acids Research* (1983), 11:6089–6105.

Zambryski, P., et al., "Ti plasmid vector for the introduction of DNA into plant cells without alteration of their normal regeneration capacity," *EMBO J* (1983), 2:2143–2150.

Zoller, M.J., et al., "Oligonucleotide–directed mutagenesis of DNA fragments cloned into M13 vectors," *Methods in Enzymology*, vol. 100, Recombinant RNA, Part B, R. Wu, et al., eds., Academic Press, Inc., N.Y. (1983), Chapt. 32:468–500.

Post–Beittenmiller M. et al., "Expression of Holo and APO Forms of Spinach Acyl Carrier Protein–1 in Leaves of Transgenic Tobacco Plants" Plant Cell vol. 1, No. 9 (1989), pp. 889–900.

Aparacio, J.F., et al., "Organization of the biosynthetic gene cluster for rapamycin in *Streptomyces hygroscopicus:* analysis of the enzymatic domains in the modular polyketide synthase." Gene, vo. 169, No. 1, Feb. 11, 1996, p. 9–16.

* cited by examiner

SEQUENCE LISTING

```
<160> NUMBER OF SEQ ID NOS: 5

<210> SEQ ID NO: 1
<211> LENGTH: 9
<212> TYPE: PRT
<213> ORGANISM: Unknown
<220> FEATURE:
<223> OTHER INFORMATION: Description of Unknown Organism: PTS2 Targeting
      Signal
<221> NAME/KEY: MOD_RES
```

-continued

```
<222> LOCATION: (2)
<223> OTHER INFORMATION: Leu, Ile or Gln
<221> NAME/KEY: MOD_RES
<222> LOCATION: (3)..(7)
<223> OTHER INFORMATION: any amino acid
<221> NAME/KEY: MOD_RES
<222> LOCATION: (8)
<223> OTHER INFORMATION: His or Gln

<400> SEQUENCE: 1

Arg Xaa Xaa Xaa Xaa Xaa Xaa Xaa Leu
 1               5

<210> SEQ ID NO: 2
<211> LENGTH: 51
<212> TYPE: DNA
<213> ORGANISM: Artificial Sequence
<220> FEATURE:
<223> OTHER INFORMATION: Description of Artificial Sequence: Synthetic
      Polylinker

<400> SEQUENCE: 2
cggatccata tgaacctcta gagaattcat agactagtcc taggtacgta g          51

<210> SEQ ID NO: 3
<211> LENGTH: 59
<212> TYPE: DNA
<213> ORGANISM: Artificial Sequence
<220> FEATURE:
<223> OTHER INFORMATION: Description of Artificial Sequence: Synthetic
      Polylinker

<400> SEQUENCE: 3
gtacctacgt acctaggact agtctatgaa ttctctagag gttcatatgg atccgagct    59

<210> SEQ ID NO: 4
<211> LENGTH: 24
<212> TYPE: DNA
<213> ORGANISM: Artificial Sequence
<220> FEATURE:
<223> OTHER INFORMATION: Description of Artificial Sequence: Synthetic
      Polylinker

<400> SEQUENCE: 4
gatccatcca ctagtcctag gtac                                         24

<210> SEQ ID NO: 5
<211> LENGTH: 20
<212> TYPE: DNA
<213> ORGANISM: Artificial Sequence
<220> FEATURE:
<223> OTHER INFORMATION: Description of Artificial Sequence: Synthetic
      Polylinker

<400> SEQUENCE: 5
gtacctagga ctagtggatg                                              20
```

PRODUCTION OF POLYKETIDES IN PLANTS

This application claims the benefit of U.S. provisional application No. 60/052,211 filed Jul. 10, 1997.

TECHNICAL FIELD

The present invention is in the field of polyketide synthesis and the production of transgenic plants. The present invention specifically provides methods for preparing plant cells and plants that express one or more functional polyketide synthases (PKS) and polyketides.

BACKGROUND ART

Polyketides are a large, structurally diverse family of natural products. Polyketides possess a broad range of biological activities including antibiotic and pharmacological properties. For example, polyketides are represented by such antibiotics as tetracyclines and erythromycin; anticancer agents including daunomycin; immunosuppressants, for example FK506 and rapamycin; veterinary products such as monensin and avermectin; and agriculturally used compounds such as spinocyn (insecticidal) and soraphen (antifungal). Polyketides are especially abundant in a class of mycelial bacteria, the actinomycetes.

Polyketide synthases are multifunctional enzymes related to fatty acid synthases (FASs). PKS catalyze the biosynthesis of polyketides through repeated (decarboxylative) Claisen condensations between acylthioesters, usually acetyl, propionyl, malonyl or methylmalonyl. Following each condensation, they introduce structural variability into the product by catalyzing all, part, or none of a reductive cycle comprising a ketoreduction, dehydration, and enoylreduction on the β-keto group of the growing polyketide chain. After the carbon chain has grown to a length characteristic of each specific product, it is released from the synthase by thiolysis or acyltransfer. Thus, PKS consist of families of enzymes which work together to produce a given polyketide. It is the controlled variation in chain length, choice of chain-building units, and the reductive cycle, genetically programmed into each PKS, that contributes to the variation seen among naturally occurring polyketides. The polyketides resulting from the reactions catalyzed by the PKS often require further modification, such as glycosylation, in order to provide antibiotic activity.

Three general classes of PKS exist. One class, known as Type I, "complex" or "modular" PKS, is represented by the PKS for macrolides such as erythromycin. The "modular" PKS are assemblies of several large multifunctional proteins carrying, between them, a set of separate active sites for each step of carbon chain assembly and modification (Cortes, J., et al., *Nature* (1990) 348:176; Donadio, S., et al., *Science* (1991) 252:675; MacNeil, D. J., et al., *Gene* (1992) 115:119). Structural diversity occurs in this class from variations in the number and type of active sites in the PKS. This class of PKS displays a one-to-one correlation between the number and clustering of active sites in the primary sequence of the PKS and the structure of the polyketide backbone. (See FIG. 1.)

The second class of PKS, called Type II or "aromatic" PKS, is represented by the synthases for aromatic compounds. The "aromatic" PKS are typically encoded by at least three separate open reading frames and have a single set of iteratively used active sites (Bibb, M. J., et al., *EMBO J.* (1989) 8:2727; Sherman, D. H., et al., *EMBO J.* (1989) 8:2717; Femandez-Moreno, M. A., et al., *J. Biol. Chem.* (1992) 267:19278). (See FIG. 2.)

A third class of PKS is generally known as "fungal" PKS and is a multifunctional protein encoded in a single reading frame. A typical "fungal" PKS is 6-methyl salicylic acid synthase (MSAS) characterized from *Penicillium patulum*. The gene has also been isolated from *Aspergillus nidulans* and from *Colletotrichum lagenarium* and a PKS having norsolorinic acid as a product from *A. nidulans*. Fujii, I., et al., *Mole Gen Genet* (1996) 253:1–10. The fungal PKS thus do not fit neatly into the categorization of aromatic versus modular and thus constitute a third group. (See FIG. 3.)

Streptomyces is an actinomycete which is an abundant producer of aromatic polyketides. In each Streptomyces aromatic PKS so far studied, carbon chain assembly requires the products of three open reading frames (ORFs). ORF1 encodes a ketosynthase (KS) and an acyltransferase (AT) active site; ORF2 encodes a protein similar to the ORF1 product but lacking the KS and AT motifs; and ORF3 encodes a discrete acyl carrier protein (ACP).

For example, *Streptomyces coelicolor* produces the blue-pigmented polyketide, actinorhodin. The actinorhodin gene cluster (act), has been cloned. The cluster encodes the PKS enzymes described above, a cyclase and a series of tailoring enzymes involved in subsequent modification reactions leading to actinorhodin, as well as proteins involved in export of the antibiotic and at least one protein that specifically activates transcription of the gene cluster. Other genes required for global regulation of antibiotic biosynthesis, as well as for the supply of starter (acetyl CoA) and extender (malonyl CoA) units for polyketide biosynthesis, are located elsewhere in the genome. The act gene cluster from *S. coelicolor* has been used to produce actinorhodin in *S. parvulus*. Malpartida, F., et al., *Nature* (1984) 309:462.

Bartel, et al., *J Bacteriol* (1990) 172:4816–4826, recombinantly produced aloesaponarin II using *S. galilaeus* transformed with an *S. coelicolor* act gene cluster consisting of four genetic loci, actI, actIII, actIV and actVII. Hybrid PKS, including the basic act gene set but with ACP genes derived from granaticin, oxytetracycline, tetracenomycin and frenolicin PKS, have also been designed which are able to express functional synthases. Khosla, C., et al., *J Bacteriol* (1993) 175:2197–2204. Hopwood, D. A., et al., *Nature* (1985) 314:642–644, describes the production of hybrid polyketides, using recombinant techniques. Sherman, D. H., et al., *J Bacteriol.* (1992) 174:6184–6190, reports the transformation of various *S. coelicolor* mutants, lacking different components of the act PKS gene cluster, with the corresponding granaticin (gra) genes from *S. violaceoruber*, in trans.

Recombinant production of heterologous functional PKS—i.e., a PKS which is capable of producing a polyketide—has been achieved in Streptomyces and hybrid forms of aromatic PKS have been produced in these hosts as well. See, for example, Khosla, C., et al., *J Bacteriol* (1993) 175:2194–2204; Hopwood, D. A., et al., *Nature* (1985) 314:642–644; Sherman, D. H., et al., *J Bacteriol* (1992) 174:6184–6190. In addition, recombinant production of modular PKS enzymes has been achieved in Streptomyces as described in PCT application WO95/08548. However, a single vector which carried genes encoding PKS catalytic sites was transformed into *E. coli* by Roberts, G. A., et al., *Eur J Biochem* (1993) 214:305–311, but the PKS was not functional, presumably due to lack of Phospho pantetheinylation of the acyl carrier proteins.

Recombinant production of functional polyketide synthases in Streptomyces hosts was also described in PCT applications WO98/01546 and WO98/01571, both published Jan. 15, 1998.

A large number of polyketide synthases have been cloned, including the PKS for the production of avermectin (U.S. Pat. No. 5,252,474); spiramycin (U.S. Pat. No. 5,098,837); and tylosin (European application publication no. 791,655 published Feb. 19, 1997).

U.S. Pat. No. 5,716,849 describes the recovery and sequencing of the nucleotide sequence encoding the PKS cluster for the production of soraphen. The disclosure, which is incorporated herein by reference, prophetically describes the expression of the soraphen PKS encoding nucleotide sequence in bacteria, yeast and plants. The disclosure indicates that the PKS proteins produced will be functional in synthesis of polyketides. However, actual expression and functionality were not demonstrated.

It is known that in order for the PKS cluster to be functional, the translated apo-PKS must be phosphopantetheinylated enzymatically to obtain holo-ACP synthase components. Carreras, C.W., et al., *Biochemistry* (1997) 36:11757–11761. The conversion from apo-PKS to PKS containing holo-ACPs requires an appropriate phosphopantetheinyl transferase (PPT). It has been recognized that PPT enzymes are members of a superfamily, but they are not interchangeable. For example, PPT enzymes which are able to convert apo-fatty acid synthase enzyme clusters to the holo-form are not effective in thus converting typical PKS apoenzymes. Lambalot, R. H., et al., *Chem and Biol* (1996) 3:923–936. The necessity for providing PPT activity in order to obtain functional PKS recombinantly in *E. coli* was described by Cox, R. J., et al., *FEBS LETT* (1997) 405:267–272. In addition, WO 98/27203, the contents of which are incorporated herein by reference, demonstrates the recombinant production of a functional 6-MSAS in yeast using a fusion protein containing the 6-MSAS from *P. patulum* and the PPT enzyme (holo-ACP synthase) from *Bacillus subtilis*, specifically surfactant holo-ACP synthase (Sfp). Production of 6-MSA in *E. coli* modified to contain an expression system for 6-MSAS, along with an expression system for the Sfp gene was also demonstrated under specified conditions.

The present invention provides plants transformed to contain a single or multivector system for the production of PKS and the resultant polyketides. The use of plants for the expression and generation of functional PKS allows a suitable source for large scale production of PKS and polyketides; in addition, the polyketides produced may confer desirable properties on the plants producing them, such as insect resistance.

DISCLOSURE OF THE INVENTION

The present invention provides methods for efficiently producing both new and known PKS and polyketides using recombinant technology and plant host/vector systems. In particular, the present invention relies on the use of plant host/vector systems to produce PKS which in turn catalyze the production of a variety of polyketides. Such polyketides are useful as: antibiotics; antitumor agents; immunosuppressants; for a wide variety of other pharmacological purposes; and for agricultural uses (such as an antifungal or insecticidal agent) either in suitable formulations or in situ in the plant in which they are produced.

In one embodiment, the invention provides genetically engineered plant cells, plants and plant parts modified to produce recombinant polyketide synthase (PKS) gene clusters. Specifically, the invention provides genetically engineered plant cells, plant parts and plants comprising:
  (a) a PKS gene cluster which encodes a PKS capable of catalyzing the synthesis of a polyketide; and
  (b) one or more control sequences operatively linked to the PKS gene cluster, whereby the genes in the gene cluster can be transcribed and translated in the genetically engineered plant cell, plant part or plant to produce a functional PKS.

In particularly preferred embodiments, the plant cells, plant parts or plant are further modified to contain phosphopantetheinyl transferases (PPT) enzymes that convert the acyl carrier protein (ACP) apoenzyme activities to holo-ACPs. These PPT enzymes may be obtained from various microbial sources as further described below.

The invention further provides methods for producing functional recombinant PKS and polyketides by culturing the plant, plant cells, etc., under conditions whereby the PKS gene clusters are expressed and functionally active; and, optionally, incubating said plant, plant cells, etc., under conditions whereby the PKS is functionally active and produces polyketides.

In a further embodiment, the invention provides methods for preparing a combinatorial polyketide library comprising:
  (a) providing a population of vectors wherein the vectors comprise a random assortment of polyketide synthase (PKS) genes, modules, active sites, or portions thereof and one or more control sequences operatively linked to said genes;
  (b) transforming a population of host plant cells or plants with said population of vectors;
  (c) culturing said population of host plant cells or plants under conditions whereby the genes in said gene cluster can be transcribed and translated, thereby producing a combinatorial library of PKS and resultant polyketides.

The invention further provides recombinant materials for the production of PKS enzymes in plant hosts and the resultant polyketides produced in the plant hosts.

MODES OF CARRYING OUT THE INVENTION

U.S. Pat. No. 5,712,146, incorporated herein by reference, describes various 5 recombinant expression systems for both modular and aromatic PKS. In addition, PCT/US97/23014, cited above and incorporated herein by reference, describes multivector systems for various PKS useful in production of functional PKS in *E. coli* and yeast as well as suitable expression systems for PPT enzyme activities functional in converting the apo-PKS enzymes produced to functionality by providing holo-ACP. It has now been found that these recombinant production systems can be used in plant hosts.

The present invention provides for the production of significant quantities of PKS and polyketides constitutively, or at an appropriate stage of the growth cycle of the plant host cell or plant. The polyketides so produced can be used as therapeutic agents to treat a number of disorders, depending on the type of polyketide in question. For example, several of the polyketides produced by the present method will find use as immunosuppressants, as anti-tumor agents, for the treatment of viral, bacterial and parasitic infections as well as in agricultural setting, such as an insecticidal or antifungal agent. The ability to recombinantly produce polyketides in plant cells also provides a powerful tool for characterizing PKS and the mechanism of their actions, as well as providing useful characteristics to the plant host.

PKS Expression Systems in General

Figure 1:
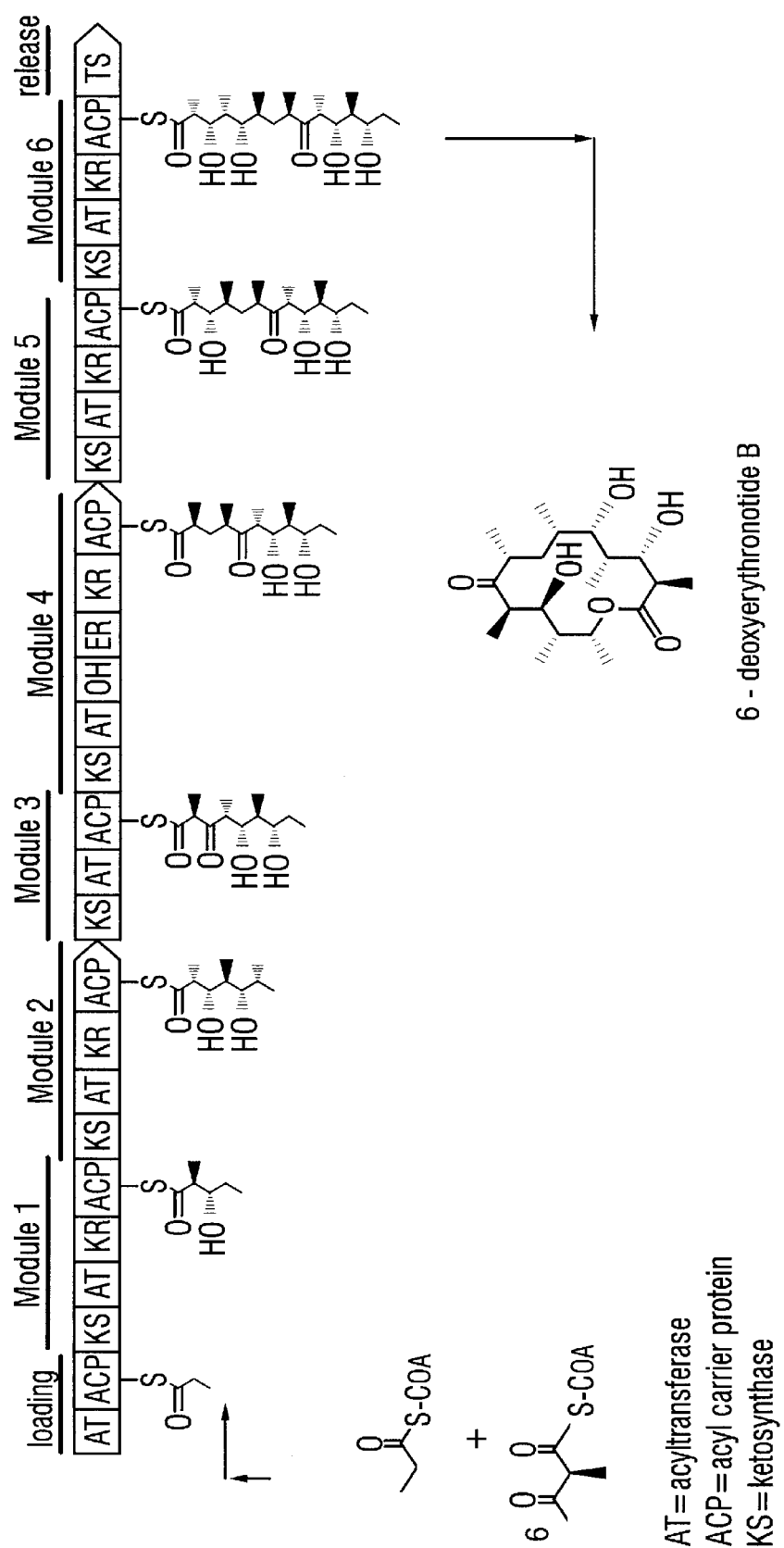
FIG. 1 is a diagram showing the organization of erythromycin PKS as typical of a modular PKS.
Figure 2:
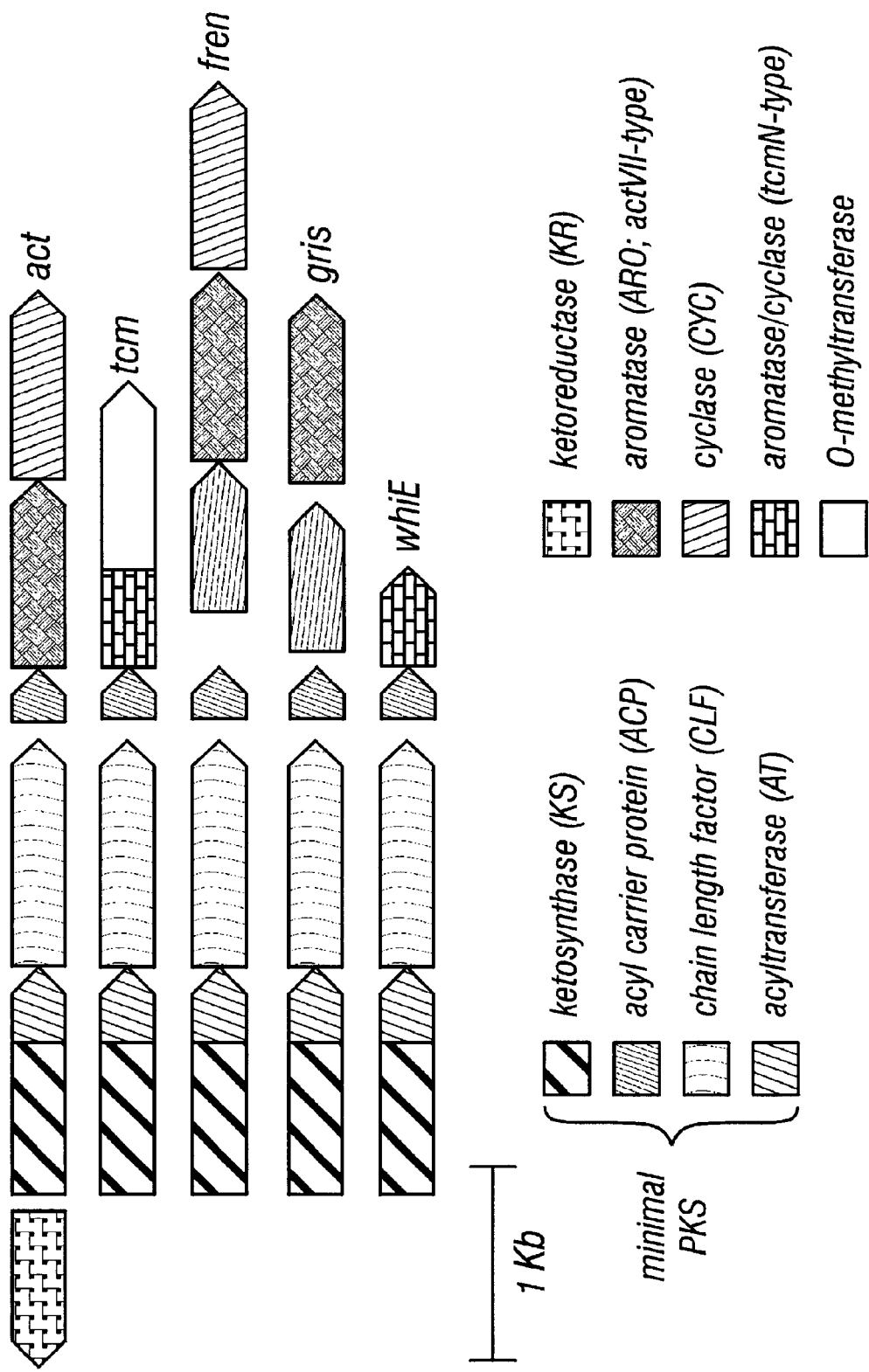
FIG. 2 is a diagram showing the composition of several typical aromatic PKS.
Figure 3:
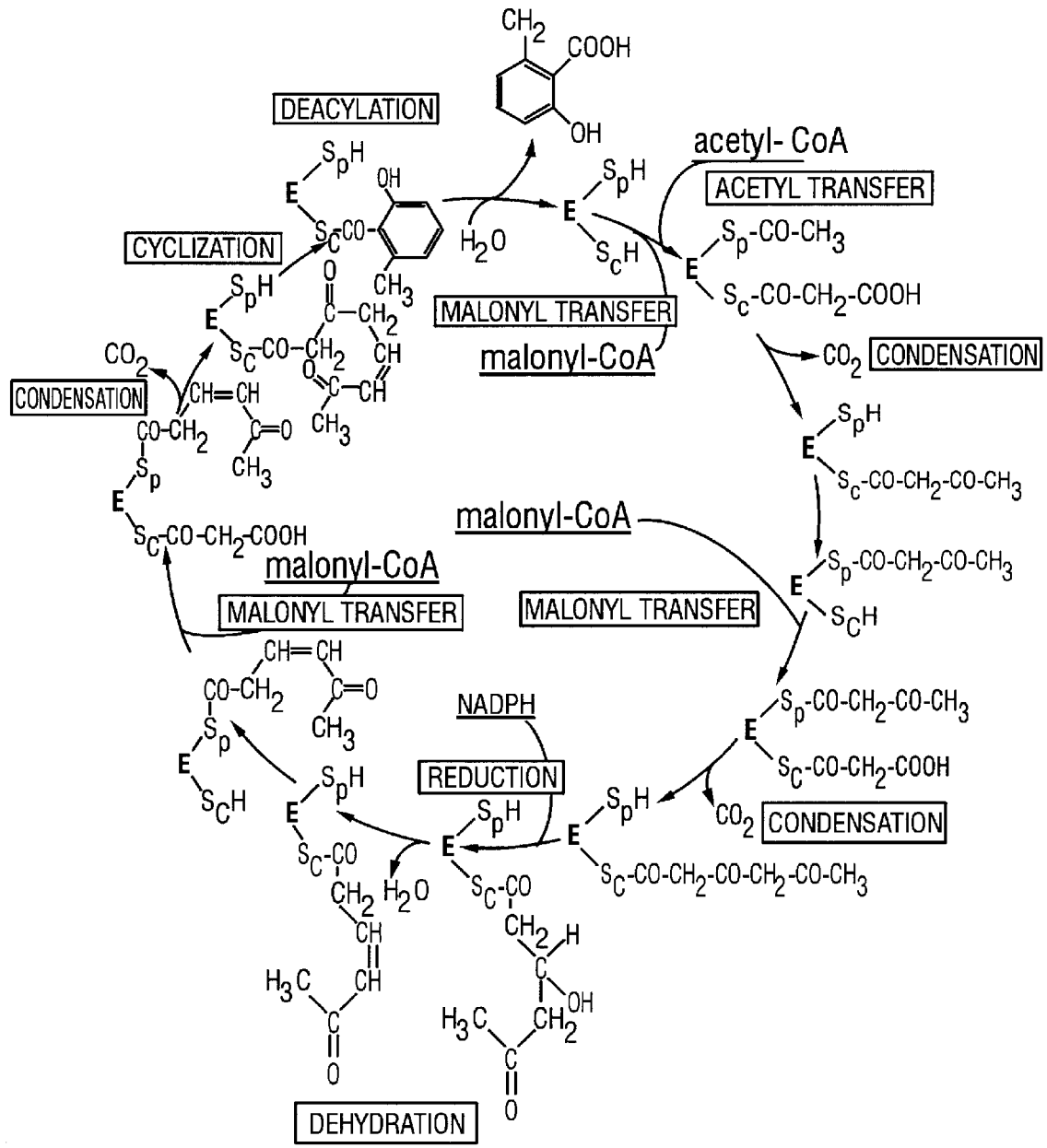
FIG. 3 is a diagram of the organization of the fungal 6-MSAS.
Figure 1:
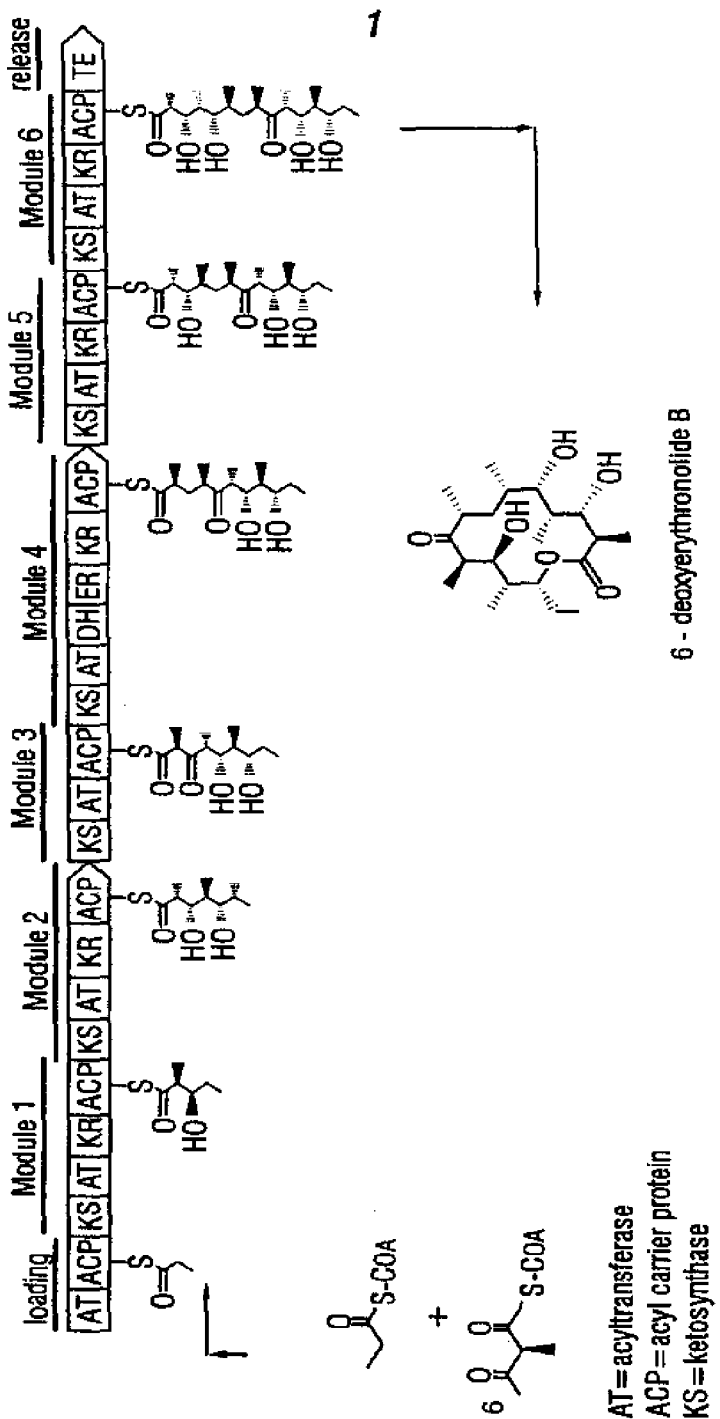
Figure 2:
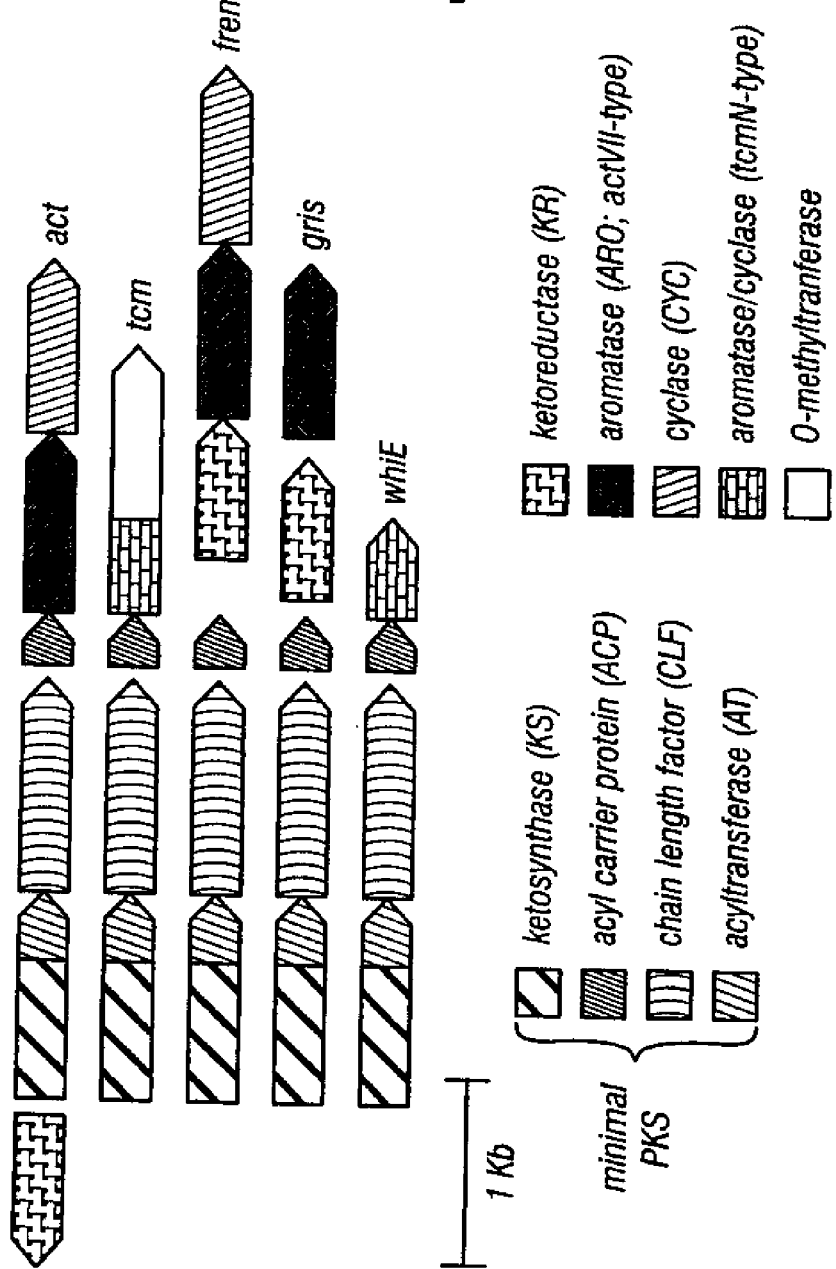
Figure 3:
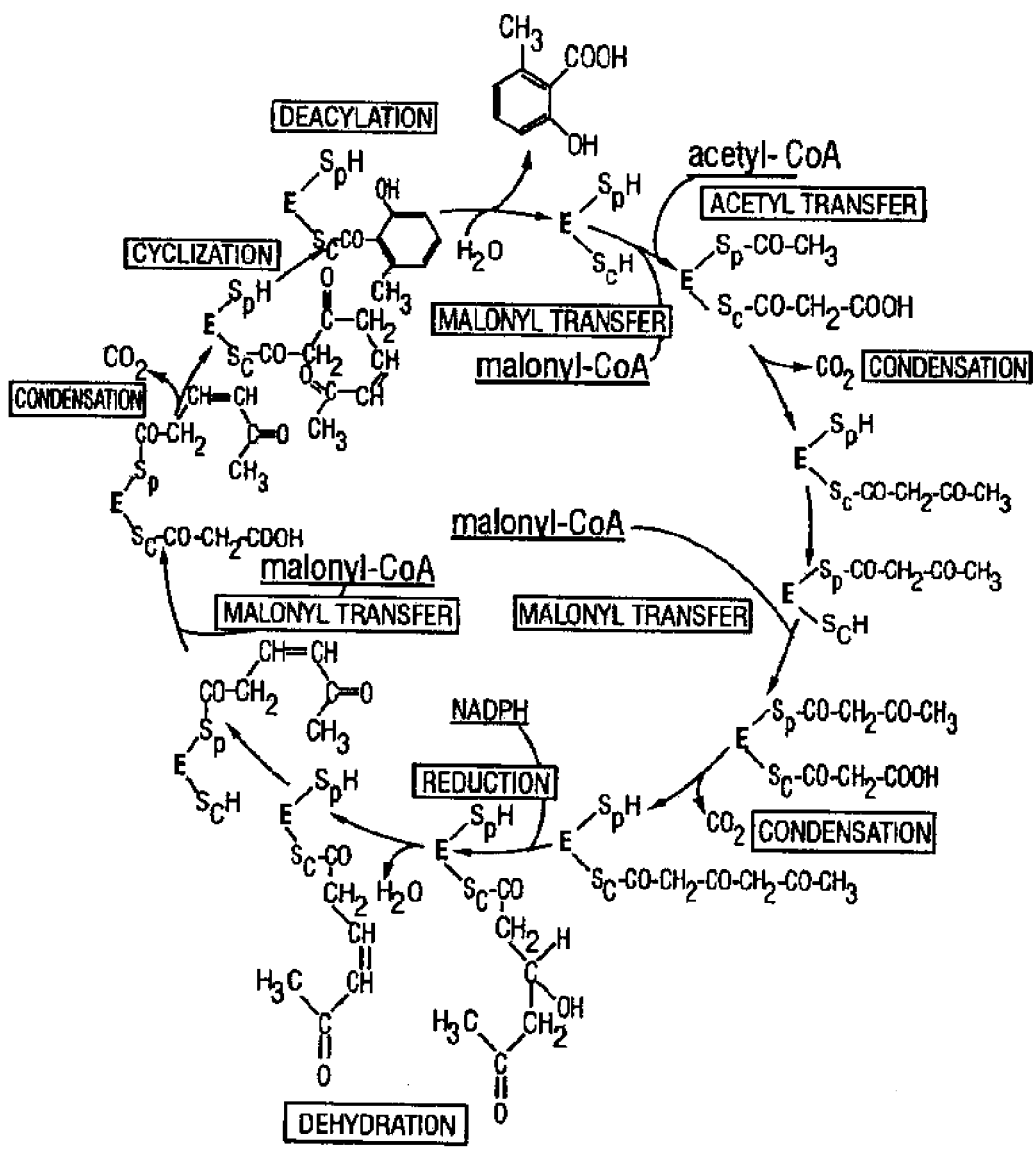

U.S. Pat. No. 5,712,146 cited above provides detailed descriptions of various known PKS expression systems and how such systems can be genetically manipulated using recombinant DNA techniques. These teachings can be applied in the present invention, with the alterations noted below, to generate recombinant plant cells and plants that express one or more PKS. A brief, but non-limiting summary, of aromatic, modular and fungal PKS systems is shown in FIGS. 1, 2 and 3, respectively and discussed below.

Aromatic PKS systems are characterized by the iterative use of the catalytic sites on the enzymes produced. In aromatic PKS systems, the enzymes of the minimal PKS are encoded in three open reading frames (ORFs). As shown in FIG. 1, the actinorhodin PKS is encoded in six separate ORFs. For the minimal PKS, one ORF contains a ketosynthase (KS) and an acyltransferase (AT); a second ORF contains a chain-length factor (CLF); and a third reading frame encodes an acyl carrier protein (ACP). Additional ORFs encode an aromatase (ARO), a cyclase (CYC), and a ketoreductase (KR). The combination of a KS/AT, ACP, and CLF constitutes a minimal PKS, since these elements are necessary for a single condensation of a two-carbon unit.

On the other hand, the grs PKS contains five separate ORFs wherein the KS/AT, CLF, and ACP are on three ORFs, the KR is on a fourth, and the ARO is on a fifth.

On the other hand, in the modular PKS systems, each catalytic site is used only once and the entire PKS is encoded as a series of "modules." A minimal module contains at least a KS, an AT and an ACP. Optional additional activities include KR, DH, an enoylreductase (ER) and a thioesterase (TE) activity as shown in FIG. 2.

The "fungal" PKS encoding 6-methyl salicylic acid synthase (6-MSAS) is in a sense similar to the aromatic PKS, although it has only one reading frame for all its activities (KS/AT, a dehydratase (DH), KR and ACP) since the sites are used iteratively, as shown in FIG. 3.

The present invention can be used to generate expression systems for the catalytic activities involved in the aromatic, modular and fungal PKS systems in plant cells, parts and whole plants.

For example, the PKS subunits of interest can be obtained from an organism that expresses the same, using recombinant methods, such as by screening cDNA or genomic libraries, derived from cells expressing the gene, or by deriving the gene from a vector known to include the same. The gene can then be isolated and combined with other desired PKS subunits, using standard techniques. If the gene in question is already present in a suitable expression vector, it can be combined in situ, with, e.g., other PKS subunits, as desired. The gene of interest can also be produced synthetically, rather than cloned. The nucleotide sequence can be designed with the appropriate codons for the particular amino acid sequence desired. In general, one will select preferred codons for the intended plant host in which the sequence will be expressed. The complete sequence is assembled from overlapping oligonucleotides prepared by standard methods and assembled into a complete coding sequence for subsequent transfer into a plant host cell. See, e.g, Edge (1981) *Nature* 292:756; Nambair, et al., (1984) *Science* 223:1299; Jay, et al., (1984) *J Biol Chem* 259:6311.

Further, the PKS proteins produced may contain the amino acid sequences and thus the substrate specificities and activities of naturally occurring forms, or altered forms of these proteins may be used so long as the desired catalytic activity is maintained. As described in U.S. Pat. No. 5,712,146, mutations can be made to the native PKS subunit sequences and such mutants used in place of the native sequence, so long as the mutants are able to function with other PKS subunits to collectively catalyze the synthesis of an identifiable polyketide. Such mutations can be made to the native sequences using conventional techniques such as by preparing synthetic oligonucleotides including the mutations and inserting the mutated sequence into the gene encoding a PKS subunit using restriction endonuclease digestion. (See, e.g., Kunkel, T. A. *Proc Natl Acad Sci USA* (1985) 82:488; Geisselsoder, et al., *BioTechniques* (1987) 5:786.)

Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located (Zoller, et al., *Methods Enzymol* (1983) 100:468). Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbalie-McFarland, et al., *Proc Natl Acad Sci USA* (1982) 79:6409. PCR mutagenesis will also find use for effecting the desired mutations.

U.S. Pat. No. 5,712,146 further describes the construction of single and multiple vector hybrid aromatic or modular PKS systems for expression in filamentous fungi, where, for example, open reading frames of actinorhodin are included in expression vectors with open reading frames from alternative aromatic systems. U.S. Ser. No. 09/073,538 filed May 6, 1998 and incorporated herein by reference describes further permutations, specifically in a modular PKS cluster, whereby a multiplicity of both known and novel polyketides can be produced in recombinant host cells. The present invention, and the Examples provided herein, extends these inventions by demonstrating the suitability of plant cell hosts and plants, to serve as a PKS expression host for the production of functional PKS and the resultant polyketides.

In addition to activities present in the PKS cluster, post-translational modifications to obtain functional PKS are also required. In particular, it is essential that the ACP function be provided with a phosphopantetheinyl moiety. The holo-ACP synthases described above are necessary for this activation. In a preferred embodiment of the present invention, holo-ACP synthases are provided to the plant cells, plant parts or whole plants using recombinant expression systems as well.

Thus, a preferred mode of practicing the present invention is to express a heterologous holo-ACP synthase enzyme along with a PKS enzyme to convert the apo-PKS into a holo-PKS with activity in vivo. As has been described by Kealey et al., *Proc Natl Acad Sci USA* (1998) 95:505–509, incorporated herein by reference, little or no polyketide product is produced by the 6-MSAS of *P. patulum* in yeast hosts unless a heterologous holo-ACP synthase is provided. This function can be provided by introduction of a separate vector expressing the holo-ACP synthase, by introduction of a single vector expressing both the holo-ACP synthase and the PKS, or by the introduction of a single gene that encodes a fusion protein between the holo-ACP synthase and the PKS.

One preferred mode of carrying out the present invention is the use of the enzyme Sfp from *Bacillus subtilis*, a phosphopantetheinyl transferase (PPTase) that is required for the production of surfactin. A recombinant Sfp gene can be incorporated either in a vector separate from that comprising the PKS gene(s), or in the same vector that comprises that PKS gene(s). Further, the coding sequence for the Sfp protein may be fused to a PKS coding sequence so that both PKS and Sfp functions are part of a single chimeric protein.

Other PPTases of use with the present invention are EntD of *E. coli* required for enterobactin synthesis (Gehring, et al., *Biochem* (1997) 36:8495–8503) and Gsp of *Bacillus brevis* required for gramicidin synthesis (Borchert, et al., *J Bacteriol* (1994) 176:2458–2462). Individual PPTases may be sufficient to posttranslationally modify multiple PKS, other PPTases may have limited substrate specificity, so that particular PPTases may be required for an individual PKS. In *E. coli* at least three different PPTases have been identified. The entD-encoded PPTase is specific for enterobactin synthase, whereas ACPS is specific for fatty acid synthase (Lambalot, et al., supra).

The PKS expression system used in the present method can be present on a single vector, or can be provided on multiple vectors. When using multiple vectors, the vectors can combine in an altered cell to from a functional PKS expression system or can be made so as to individually express each element of the PKS system to provide each of the enzymatic activities needed for polyketide synthesis. Both of these approaches are described in U.S. Pat. No. 5,712,146 and PCT application US97/23014. In a single vector system, a single vector contains all the enzymatic elements of the PKS. In a multiple vector system, the catalytic activities of the PKS expression system are separated onto different vectors, which, after introduction into a plant host cell, can either recombine to form a single PKS expression system or can be expressed using separate expression control elements to form the PKS. While a single vector approach is more efficient at producing functionally active PKS, the multiple vector approach has the advantage of being able to be used to generate a library of PKS, each one having a different enzymatic activity. Where multiple vectors are used, it is possible, in some instances, to provide vectors for various portions of the cluster in different plants which can then be cross-bred to obtain a complete desired expression system. Further, components of the cluster, and indeed, posttranslational enzymes may be encoded in a single reading frame to obtain a fusion protein. Fusions providing a modular PKS cluster as well as a holo-ACP synthase are described in the above-referenced PCT application.

In constructing vectors for production of aromatic PKS systems, the separate reading frames, such as those shown in FIG. 2, may be incorporated on a single vector or, if properly constructed, each of the reading frames can be distributed among more than one vector, each with appropriate sequences for effecting control of expression in a plant host cell or recombination amongst the reading frames. For modular systems a single module or more than one module may reside as a part of an expression system on a single vector or multiple vectors can be used to modify the plant cell to contain the entire desired PKS system.

In addition to the PKS encoding sequences, it is preferred to introduce other protein expression systems into the plant host to effect Phospho pantetheinylation. As stated above, the expression system for the appropriate PPT enzyme may be on the same or different vector(s) as the vector(s) which carry the PKS cluster expression system or the PPT enzyme may be produced as a fusion protein with part or all of a PKS.

For expression in plants, specifically, the PKS and post-translational processing enzyme expression systems may be modified to utilize codons preferred in plants, to eliminate cryptic splice sites, to alter the GC/AT content and the like. Suitable modifications to nucleotide sequences that do not result in changes in the amino acid sequence encoded are understood in the art.

Additional enzymes such as glycosylation enzymes that effect post translational modifications to the polyketides may also be introduced into the plant host through suitable recombinant expression systems.

In one illustrative embodiment three separate vectors are employed to produce a modular PKS. Each vector permits the construction of 64 different open reading frames using two extender ATs (one from methylmalonyl CoA and the other from malonyl CoA) and the four combinations involving KR, DH, and ER as described above. Thus, module No. 1 may employ malonyl CoA as an extender unit; module No. 2 methylmalonyl CoA; the opposite sequence can be used, or both extenders might use malonyl CoA or both might use methylmalonyl CoA. This results in four separate types of extender combinations, each of which is multiplied by the four KR/DH/ER variants. Each separate plasmid offers the same set of possibilities; one of the plasmids must also contain a loading function and one must contain a thioesterase function. Thus, by construction of 192 plasmids, the upper limit of synthesis of novel polyketides is 64×64×64 or 262,144 molecules, providing an efficient method to obtain large numbers of novel polyketides.

Expression Units to Express Exogenous DNA in a Plant

As provided above, the present invention employs expression units (or expression vectors, systems or modules) to express an exogenously supplied PKS encoding DNA molecule in a plant cell or a plant regenerated therefrom. Methods for generating expression units/systems/vectors for use in plants are well known in the art and can readily be adapted for use in expressing PKS encoding sequences. Typically, as described above, such units employ a PKS encoding module and one or more expression control elements. The choice of the control elements employed will be based on the plant that is to be altered, the level of control over expression that is desired and the transformation system used. A skilled artisan can readily use any appropriate plant/vector/expression system in the present methods following art known methods and the outline provided herein. In the Examples, the construction of several suitable plant expression vectors is described.

The expression control elements used to regulate the expression of a PKS coding sequence will typically be a heterologous expression control element, one that is not normally associated with the PKS encoding sequence. However, homologous control elements, ones that are normally associated with the PKS encoding sequence, can be used if active in the chosen plant host. A variety of heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 35S promoter, to control gene expression in a plant. Lastly, plant promoters such as prolifera promoter, fruit-specific promoters, Ap3 promoter, heat shock promoters, seed-specific promoters, etc., can also be used. The most preferred promoters will be active in stages of plant cell growth or development so that PKS production is specific for a tissue or plant organ, for example in leaf tissue, seeds or fruiting bodies.

Either a constitutive promoter (such as the CaMV or Nos promoters), an organ-specific promoter (such as the E8 promoter from tomato) or an inducible promoter is typically ligated to the PKS coding region using standard techniques known in the art. The expression unit may be further optimized by employing supplemental elements such as transcription terminators and/or enhancer elements.

Thus, for expression in plants, the expression units will typically contain, in addition to the PKS coding sequence, a plant promoter region, a transcription initiation site and a transcription termination sequence. As shown in the Examples, unique restriction enzyme sites at the 5' and 3' ends of the expression unit are typically included to allow for easy insertion into a preexisting vector.

In the construction of heterologous promoter driven expression system, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression system/unit can also contain a transcription termination region downstream of the structural gene to provide for efficient termination. The termination region may be obtained from the same gene as the promoter sequence or may be obtained from different genes. If the mRNA encoded by the PKS encoding sequence is to be efficiently processed, DNA sequences that direct polyadenylation of the RNA are also commonly added to the vector construct. Polyadenylation sequences include, but are not limited to, the Agrobacterium octopine synthase signal (Gielen et al., *EMBO J* 3:835–846 (1984)) or the nopaline synthase signal (Depicker et al., *Mol and Appl Genet* 1:561–573 (1982)).

The resulting expression unit is ligated into or otherwise constructed to be included in a vector which is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

In a particularly preferred embodiment of the invention, the plant cell or plant can be made self-screening by introducing a polyketide-responsive receptor that is intracellular to or is displayed at the surface of the plant host cell producing the polyketide itself. This "autocrine" system allows the colonies to self-select for those activating the receptor. Such systems are described, for example, in an article by Broach, J. R., et al., *Nature* (1996) 384:Supp.7:14–16.

Autocrine systems need not be limited, however, to receptors, but can include proteins that are expressed internal to the transformed plant cell and whose interaction can be evaluated with respect to the polyketides produced, in a manner analogous to the yeast 2 hybrid system described by Fields in U.S. Pat. No. 5,283,173.

Thus, the plant cells can be modified to create "plant cell-based detection systems for polyketide function." The function of the polyketide may include agonist or antagonist activity with respect to a receptor which is either produced at the surface of the cell or produced intracellularly, or the polyketides may be agonists or antagonists for two hybrid interaction screens so that it will be possible to select for protein-protein interaction inhibitors or cross-linking factors analogous to rapamycin and FKS506.

Compartmentalization of Enzymatic Activities

Polyketide synthases can utilize a range of different acylCoA precursors in the synthesis of a polyketide product. These include acetylCoA, malonylCoA, propionylCoA and methylmalonylCoA, which are used commonly in many biosynthetic pathways. In addition, more specific acylCoA derivatives can be used either as initial precursor for the synthesis or as an extender precursor later during the synthetic cycle. The abundance of the commonly used precursors is not well understood in plants. However, the level of these precursors is expected to vary between different cellular compartments. Polyketide product synthesis with any specific PKS consequently is expected to vary between the compartments. Any subcellular compartment that is a typical site for catabolic and anabolic functions could be used as the site for polyketide synthesis, including the cytosol, plastids, peroxisomes, mitochondria, etc.

Although any compartment may be used with any PKS, depending upon other functions that may be expressed along with the PKS, some compartments may be more preferred for syntheses with specific precursors. For example, for PKS-catalyzed reactions that require only acetylCoA and malonylCoA as precursors (e.g., fungal PKS), preferred compartments are the cytosol and the plastid, with the most preferred compartments being the plastid. Plastids are the site of fatty acid synthesis, and as such are expected to contain the highest levels of acetylCoA and malonylCoA of any cellular compartment. Nawrath, et al., *Proc Natl Acad Sci USA* (1994) 91:12760–12764 have reported 5- to 10-fold increased rates of heterologous synthesis of polyhydroxybutyrates in plant cells using plastid-targeted enzyme activities rather than cytosolic activities. The only precursor required for the heterologous synthesis of polyhydroxybutyrates is acetylCoA.

The availability of propionylCoA and methylmalonylCoA in the different compartments is not presently known in plant cells. There has been one report that methylmalonylCoA exists in some plant cells (Schröder, J., et al., *Biochemistry* (1998) 37:8417–8425 incorporated herein by reference), based on its requirement for the synthesis of a C-methylated chalcone in *Pinus strobus*. PropionylCoA, which is produced during the catabolism of odd-chain-length fatty acids and certain amino acids, may be present in oxidative compartments such as the mitochondrion or the peroxisome. During some stages of plant development, these compartments are expected to contain high levels of acetylCoA through fatty acid catabolism. As these compartments are not involved in biosynthesis, malonylCoA is not expected to be present at significant levels.

The targeting of gene products to specific subcellular compartments in eukaryotic cells, and particularly in plant cells, has been studied extensively. For example, U.S. Pat. Nos. 5,728,925 and 5,717,084 (incorporated herein by reference) describe means by which proteins can be targeted to chloroplasts. Generally chloroplast targeting can be achieved by the addition of a transit peptide to the N-terminus of a cytosolic protein. The range of different sequences, and general features of said sequences, that can function as transit peptides for the plastid are well known in the art.

Methods for targeting proteins to peroxisomes are also well known in the art, and likewise utilize specific sequences of the protein synthesized in the cytosol. Peroxisomal matrix-targeted proteins can be directed into peroxisomes using either of two different types of targeting signals, either type 1 or type 2 PTS. The PTS1 is a noncleaved tripeptide motif residing at the extreme C-terminus exemplified by SKL (in single amino acid notation), with other tripeptides using the small-basic-hydrophobic amino acid motif (see Gietl, C. *Physiol Plant* (1996) 97:599–608; Olsen, et al.,*Ann Rev Plant Physiol and Plant Mol Biol* (1995) 46:123–46). The PTS2 is a nonapeptide of the form (SEQ ID NO:1) R-L/I/Q-$X_5$-H/Q-L, which is found in the N-terminal region of some peroxisomal matrix-destined proteins.

Methods for targeting proteins to mitochondria are also well known in the art.

Mitochondrial-targeted proteins are synthesized as cytosolic precursors with an N-terminal presequence. The presequence interacts with receptor proteins that initiate the process by which proteins are escorted across the outer membrane, and perhaps the inner membrane, and into various subcompartments of the mitochondrion. Sequences are also known in the art that function to target precursor polypeptides to both mitochondria and chloroplasts (e.g., WO95/08633). In order to enter the mitochondrion or other compartments large proteins may require enhanced expression of additional functions for unfolding (e.g., chaperonins). For example, mhsp7O acts inside the mitochondrion to assist the movement of proteins across the outer mitochondrial membrane (Matouschek, et al., *EMBO J* (1997) 16:6727–6736). Functions such as mitochondrial import-stimulating factor (MSF) have been implicated in the process of protein unfolding in the cytosol prior to association with mitochondrial protein import receptors (Komiya, et al., *EMBO J* (1997) 16:4267–4275).

Precursor Production

Precursor availability may be limiting for the synthesis of certain polyketide products. To increase the production level of a specific polyketide product it may be necessary to provide additional gene constructs that encode enzymes necessary for the increased synthesis of specific precursors. For example, to increase the amount of malonylCoA the enzyme acetylCoA carboxylase (ACCase), which catalyzes the conversion of acetylCoA directly into malonylCoA, can be expressed in a suitable compartment. ACCase in plants has also been reported to effect the conversion of propionylCoA to methylmalonylCoA. The utility of ACCase activity will depend upon the availability of the appropriate substrates, acetylCoA and propionylCoA. When expressed at suitable levels in compartments (and tissues) in which acetylCoA is being generated, ACCase can provide for balanced amounts of acetylCoA and malonylCoA as substrates for suitable polyketides. Alternatively, when both acetylCoA and propionylCoA are present, suitable expression of ACCase can provide for the synthesis of suitable amounts of acetylCoA, propionylCoA, malonylCoA and methylmalonylCoA.

To provide for the enhanced synthesis of methylmalonylCoA specifically, a propionylCoA carboxylase activity can be expressed in the desired compartment. An enzyme with propionylCoA-specific carboxylase activity has been identified in *Streptomyces coelicolor* A3(2) (Bramwell, et al., *Microbiology* (1996) 142(Pt3):649–655), and one of the subunits of the heterodimeric enzyme has been cloned. Through suitable expression levels of the two different carboxylases, levels of precursors suitable to a range of different polyketide biosynthetic pathways can be established in different compartments.

As plants do not generally utilize amino acids as an energy source, the level of propionylCoA may need to be enhanced for the synthesis of certain polyketides. Since propionylCoA results from the catabolism of certain amino acids, increased synthesis of a specific amino acid that leads to an increase in the intracellular concentration of that amino acid may direct increased flux through the amino acid catabolic pathway. Since biosynthetic pathways are often under feedback regulation, disruption of the feedback regulatory site of a biosynthetic enzyme can be sufficient to provide for increased amino acid concentration intracellularly. Increased amino acid concentration in plant cells has been demonstrated by mutating acetolactate synthase to relieve feedback inhibition.

Schroder, et al., *Biochemistry* (1998) 37:8417–8425 have described a biosynthetic reaction in *Pinus strobus* that required methylmalonylCoA as a substrate, and which apparently occurs in the cytosolic compartment. This reaction is part of the biosynthesis of a C-methylflavone. A few other plants have been shown to produce C-methyl flavones, derivatives of the chalcones that are produced by PKS unrelated to bacterial and fungal PKS. Based on structural analysis, it is inferred that methylmalonylCoA is a substrate in the synthesis of these different C-methyl flavones. Clearly, certain plants can synthesize methylmalonylCoA. Based on methods known in the art, it is possible to identify the genes for the biosynthesis of methylmalonylCoA and introduce these into desired host plants to provide for the synthesis of methylmalonylCoA. It may be possible to obtain genes for the synthesis of propionylCoA from the C-methyl flavone producers as well.

Tissue Type and Development Stage

During certain developmental stages or in specific tissue types plants utilize specialized metabolic functions. In certain cases substrate concentrations are enhanced to provide for the metabolic load. For example, during development and maturation of oilseeds, very high rates of fatty acid synthesis are exhibited, accompanied by increased flux of acetylCoA and malonylCoA. Oilseeds may be desired target sites for polyketide synthesis when the goal is purification of a polyketide for pharmaceutical or agricultural use. PKS, enzymes required for posttranslational modification, and other enzymes required for polyketide synthesis can be programmed for expression with suitable promoters that have specifically high activity in desired target tissues. Such tissue-and developmental stage-specific promoters are well known in the art.

Accessory Functions

A functional PKS in a plant subcellular compartment that has suitable levels of biosynthetic substrates can provide for the synthesis of a polyketide product. Most primary polyketide products are not biologically active. Generally, additional biosynthetic enzymes are required to convert the primary polyketide into a biologically active molecule.

A wide range of accessory functions has been described that are necessary to convert primary polyketides into biologically active molecules. These include cyclization reactions, oxidation reactions, reduction reactions, methylation reactions (at oxygen or carbon atoms), decarboxylation reactions, dehydration reactions, desaturase reactions, and ligation reactions. The number of steps required ranges considerably; for example, at least 10 reactions are required to convert a primary polyketide product into the potent mycotoxin aflatoxin (Brown, et al., *Proc Natl Acad Sci USA* (1 996) 93:1418–1422).

As one example, milbemycins and avermectins are polyketides with acaricidal and nematocidal activity. These compounds are produced by *Streptomyces avermitilis* and *Streptomyces hygroscopicus* subsp. *aureolacrimosus* using modular PKS. The primary polyketide product for both milbemycins and avermectins requires 12 modules, located on four distinct proteins, with expected molecular masses of 450, 700, 610 and 540 kDa (Ikeda, H., et al., *Chem Rev* (1997) 97(7):2591–2609). These modules differ only in the starter acylCoA specificity, and in the presence of a double bond at C22-C23 of avermectins. The principal differences between these classes of polyketide products is that milbemycin synthesis begins with a more common acylCoA than does avermectin (acetylCoA or propionylCoA), and milbemycins lack the disaccharide moiety attached to the C13 hydroxyl of the avermectin aglycone. The synthesis of milbemycins requires additional functions to cyclize the furan ring, and for reduction of the C5 keto group. The synthesis of avermectins requires additional functions for the synthesis of the disaccharide and its attachment to the core polyketide. All the genes necessary for the synthesis of milbemycin can be isolated from the producing organism and engineered for heterologous expression plant cells.

As a second example, strobilurin A is a fungal polyketide product, produced by certain basidiomycetes (e.g., *Strobilurus tenacellus*). Although the fill biosynthetic pathway has not been elucidated, several additional enzymes are needed in addition to the core PKS: one or two enzymes for the conversion of cinnamylCoA to benzoylCoA as the starter molecule, an enzyme for the rearrangement of the C1 COOH to C3, a C-methyltransferase and two O-methyltransferases.

The biosynthetic genes required for the synthesis of both bacterial and fungal polyketide products are generally clustered in the genomes of the producing organisms. This has been well documented for the polyketide products of the streptomycetes (Chater, K., et al., *EMBO J* (1985) 4:1893) as well as for the polyketide products of filamentous fingi (e.g., aflatoxin, Brown, et al., op cit.). Heterologous PKS probes have been used to identify genomic clones containing the PKS from any uncharacterized producer organism. As PKS clusters are fairly divergent in their nucleotide sequences, it will at times be of use to prepare homologous PKS probes through the polymerase chain reaction using degenerate primers targeted to conserved regions of PKS genes. Large genomic clones (using lambda phage, cosmids, BACs, or other vectors known to practitioners of the art) will include accessory genes in addition to the PKS detected directly by hybridization.

Transformation of Plant Cells

When an appropriate vector is obtained, for example as described above, transgenic plants are prepared which contain the desired expression unit. As described in the Examples, one method of transformation relies on vacuum infiltration to introduce the PKS encoding DNA vector into cells comprising the seed formation organs in a plant (Bechtold, N., Ellis, J., and Pelletier, G. (1993) C.R. Acad. Sci., Paris/Life Sciences 316:1194–1199). In the vacuum infiltration method, whole plants are contacted with a solution containing transformed Agrobacterium under vacuum. The plants are then allowed to further grow and develop to form seeds. The seeds are then collected and screen for the presence of the introduced vector. This method has the advantage of not needed to rely on somatic embryogenesis to regenerate plants from cultured plant cells.

In another transformation method, the vector is microinjected directly into plant cells by use of micropipettes to mechanically transfer the recombinant DNA into the plant cell (Crossway, *Mol Gen Genetics* (1986) 202:179–185). In another method, the genetic material is transferred into the plant cell using polyethylene glycol (Krens, et al., *Nature* (1982) 296:72–74), or high velocity ballistic penetration by small particles with the nucleic acid either within the matrix of small beads or particles, or on the surface, is used (Klein, et al., *Nature* (1987) 327:70–73). In still another method protoplasts are fused with other entities which contain the DNA whose introduction is desired. These entities are minicells, cells, lysosomes or other fusible lipid-surfaced bodies (Fraley, et al, *Proc Natl Acad Sci USA* (1982) 79:1859–1863).

DNA may also be introduced into the plant cells by electroporation (From in et al., *Proc Natl Acad Sci USA* (1985) 82:5824). In this technique, plant protoplasts are electroporated in the presence of plasmids containing the expression vector. Electrical impulses of high field strength reversibly permeabilize biomembranes allowing the introduction of the plasmids. Electroporated plant protoplasts reform the cell wall, divide, and regenerate.

For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

PKS encoding genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (St. Schell, J., *Science* (1987) 237:1176–1183). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema, et al., *Nature* (1983) 303:179–180). The transferred DNA region can be increased in size by the insertion of heterologous DNA without its ability to be transferred being affected. Thus a modified Ti or Ri plasmid, in which the disease-causing genes have been deleted, can be used as a vector for the transfer of the gene constructs of this invention into an appropriate plant cell.

Construction of recombinant Ti and Ri plasmids is well known in the art and, in general, follows methods typically used with the more common bacterial vectors, such as pBR322 (for example see Koncz, C., and Schell, J. (1986), *Molecular and General Genetics* 204:383–396). Additional use can be made of accessory genetic elements sometimes found with the native plasmids and sometimes constructed from foreign sequences. These may include but are not limited to "shuttle vectors," (Ruvkum and Ausubel, *Nature* (1981) 298:85–88), promoters (Lawton et al., *Plant Mol Biol* (1987) 9:315–324) and structural genes for antibiotic resistance as a selection factor (Fraley et al., *Proc Natl Acad Sci USA* (1983) 80:4803–4807).

There are two classes of recombinant Ti and Ri plasmid vector systems now in use. In one class, called "cointegrate," the shuttle vector containing the gene of interest is inserted by genetic recombination into a non-oncogenic Ti plasmid that contains both the cis-acting and trans-acting elements required for plant transformation as, for example, in the pMLJ1 shuttle vector of DeBlock et al., *EMBO J* (1984) 3:1681–1689 and the non-oncogenic Ti plasmid pGV3850 described by Zambryski et al., *EMBO J* (1983) 2:2143–2150. In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* (1984) 12:8711–8721 and the non-oncogenic Ti plasmid PAL4404 described by Hoekma, et al., *Nature* (1983) 303:179–180. Some of these vectors are commercially available.

There are two common ways to transform plant cells with Agrobacterium: cocultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Most dicot species can be transformed by Agrobacterium as all species which are a natural plant host for Agrobacterium are transformable in vitro. Monocotyledonous plants, and in particular, cereals, are not natural hosts to Agrobacterium. Attempts to transform them using Agrobacterium have been unsuccessfiil until recently (Hooykas-Van Slogteren et al., *Nature* (1984) 311:763–764). However, there is growing evidence now that certain monocots can be transformed by Agrobacterium. Using novel experimental approaches cereal species such as rye (de la Peña, et al., *Nature* (1987) 325:274–276), maize (Rhodes et al, *Science* (1988) 240:204–207), and rice (Shimamoto, et al., *Nature* (1989) 338:274–276) may now be transformed.

As described above, the identification of transformed cells or plants is generally accomplished by including a selectable marker in the transforming vector, or by obtaining evidence of successful bacterial infection.

Regeneration of Transformed Plants

Plant cells that have been transformed to contain a PKS encoding sequence can also be regenerated using known techniques. For example, plant regeneration from cultured protoplasts is described in Evans et al., *Handbook of plant Cell Cultures*, Vol. 1: (MacMillan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Using the foregoing procedures, a wide variety of plants can be transformed and regenerated. Illustrated below are arabidopsis and tobacco. Other useful species are peas, peppers, petunias, corn, wheat, and cotton. The list is nonlimiting, and any desired higher plant can be utilized as a host.

The following examples are intended to illustrate but not to limit the invention.

EXAMPLE 1

Construction of Expression Vectors for 6-MSAS

A synthetic polylinker was designed to facilitate cloning of polyketide synthase genes into the expression vector pBI121. This polylinker contains SacI, BamHI, NdeI, XbaI, EcoRi, AvrII, SpeI, SnaBI, and Asp718 restriction sites (SEQ ID NOS:2 &3):

5'-CGGATCCATATGAACCTCTAGAGAATTCATAGA-
CTAGTCCTAGGTACGTAG-3'

3'-TCGGATCCTAGGTATACTTGGAGATCTCTTAAGT-
ATCTGATCAGGATCCATGCATCCATG-5'

This polylinker was cloned into the SacI/Asp718 sites of pBlueScript (Stratagene) to produce the cloning vector 131a.

A synthetic polylinker having BamHI, AvrII, SpeI, and SnaBI restriction sites was designed (SEQ ID NO:4 & 5):

5'-GATCCATCCACTAGTCCTAGGTAC-3'
3'-GTAGGTGATCAGGATCCATG-5'

This polylinker was cloned into the BamHI/SnaBI sites of pBI121 (Clontech) to produce the expression vector 131b.

A 5.5-kbp NdeI/XbaI fragment containing the gene for the *Penicillium patulum* 6-methylsalicylic acid synthase was isolated from pDB102 (isolated from *E. coli* SCS 110) and cloned into the NdeI/XbaI sites of 131a. A BamHI/SpeI fragment from this intermediate plasmid was cloned into the BamHI/SpeI sites of 131b to give expression vector 131c which contains an expression system for 6-MSAS.

EXAMPLE 2

Construction of an Expression Vector for eryA-1

An 11.2-kbp NdeI/EcoRI fragment containing the eryAI gene from *Saccharopolyspora erythraea* fused with the DEBS thioesterase (Kao, C.M., et al., *J Am Chem Soc* (1995) 117:9105–06) was isolated from pCJT75 and cloned into the NdeI/EcoRI sites of vector 131a. A BamHI/AvrII fragment from this intermediate plasmid was cloned into the BamHI/AvrII sites of 131b to give expression vector 131d for eryA-1.

EXAMPLE 3

Construction of an Expression Vector for grsA

An NcoI/HindIII fragment containing the grsA gene from *Bacillus brevis* was isolated from pQE60-PheAT and cloned into the NcoI/HindIII sites of 131a. A XbaI/SpeI fragment from this intermediate plasmid was cloned into the XbaI/SpeI sites of 131b to give expression vector 131e for grsA.

EXAMPLE 4

Transformation of Arabidopsis using Vacuum Infiltration

Plant Growth:

1. Grow plants of the appropriate genotype to a stage at which bolts are just emerging.

Preferably, from 12–15 plants are grown in a 3.5" pot. The pot can be covered with nylon window screen after planting. Plants will grow through the screen so that when pot is inverted for infiltration less dirt falls out.

2. Clip off emerging bolts to encourage growth of multiple secondary bolts.

Emerging bolts are clipped off, for example by using scissors, to stimulate growth of multiple secondary bolts.

Vacuum Infiltration:

3. A liquid culture of Agrobacterium carrying the appropriate PKS expression vectors, such as 131c, 131d or 131e, is grown overnight. For example, a 25 ml overnight (LB+antibiotics) is started two to three days before the vacuum infiltration procedure is to be performed and is used as a starter culture. This culture is then added to 400 ml of LB+antibiotic the day before infiltration.

4. After growth for approximately 24 hours, the cells are harvested by centrifugation (for example using 5K rpm for 10 min. in a GSA rotor, preferably at room temp.) and resuspended in 3 volumes infiltration medium (OD600 approx. 0.8). [Preferably, the cells are first resuspended in a small volume and dilute to give an OD600 of ~0.8.] About 2 liters of bacteria are needed to fill a vacuum tank which is set up to transform a flat of Arabidopsis.

5. Add Agrobacterium (in infiltration medium: 1/2× Murashige & Skoog salts, or MS salts+organics; 1×B5 vitamins; 5.0% Sucrose; .044 µM Benzylamino Purine (10 µl per liter of a 1 mg/ml stock in DMSO)) to a dish or beaker and invert plants (pot, soil, and all) into liquid solution (submerge the bolts and entire rosettes in the infiltration media).

6. Place beaker into bell jar. Draw a vacuum until bubbles form on leaf and stem surface and solution starts to bubble a bit, then release vacuum very rapidly.

The necessary time and vacuum pressure will vary lab-to-lab. Good infiltration is visibly apparent as uniformly darkened, water-soaked tissue.

7. Remove plants from beaker and cover with plastic wrap or a dome to maintain humidity. The next day, uncover plants.

Cover with large humidity dome until the evening to protect the plants from direct light immediately after the infiltration. Remove the humidity dome as soon as possible to minimize growth of saprophytes 8. Grow approximately four weeks, keeping bolts from each pot together and separated from neighboring pots.

Selection of Transformants:

9. When siliques on plants are very dry, harvest seed (all seed from one pot together).

For Kanamycin selection:

10. Pour selection plates (½×Murashige & Skoog salts; 0.8% Agar; Autoclave, cool, then add: 1×B5 vitamins; Antibiotic (such as Km 50 µg/ml); Plastic 150×15 mm petri dishes are convenient (Murashige, T., et al., (1962) *Physiologia Plantarum* 15:473–497)).

11. Sterilize seed. A variety of sterilization protocols can be used. For example: a 1 minute in ethanol or isopropanol, followed by 5 minutes in 50% Bleach/50% water/0.05% Tween and then 3 rinses with sterile water.

12. Plate seed by resuspending in sterile, room temperature 0.1% agarose and spreading onto selection plates. Dry plates in laminar flow hood until seed no longer flows when plate is tipped. Use one ml agarose for every 500–1000 seed.

Plate 2000 to 4000 seed per 150×15 mm plate. Higher densities can make antibiotic selection less effective.

13. Vernalize plates for two nights in cold room. Move plates to growth chamber.

14. After about 7 days, transformants should be clearly identifiable as dark green plants with healthy green secondary leaves and roots that extend over and into the selective medium.

15. Transplant plantlets to soil, grow, and collect seed. Transplanting success is improved by breaking up agar around root prior to pulling, by removing any adhering chunks of agar from root before planting, by saturation of soil with water after transplanting, and by growing plants under a dome (for high humidity) for the first day or two. If the root is broken, put plantlet onto a new selection plate for a few days before transplanting.

EXAMPLE 5

Construction of Additional Expression Vectors

A 700 bp NcoI/XbaI fragment containing the coding sequence for Sfp from *Bacillus subtilis* was isolated from pKOS018-88A. This fragment was ligated with a 4.1 kbp NcoI-XbaI fragment containing a pUC replicon, ampicillin resistance gene, an e35S promoter (Kay, R., et al., *Science* (1987) 236:1299–1302) and Cab22L leader ending at the NcoI site and a nopaline synthase 3' fragment beginning at the XbaI site. The resulting expression vector pBH1000 contains a chimeric e35S-Sfp-nos3' gene.

A 1.7 kbp BamHI/BglII fragment containing the chimeric e35S-Sfp-nos3' gene was isolated from pBH1000. This fragment was inserted into the BamHI site of pAR4741, which contains a pACYC184 replicon (Chang, A. C. Y., et al., *J Bacteriol* (1978) 134:1141–1156), a pVS1 replicon (Itoh, Y., et al., *Plasmid* (1984) 11:206–220), the tetA gene of Tn1721 (Waters, S. H., et al., *Nucleic Acids Research* (1983) 11:6089–6105), and T-DNA border fragments (van den Elzen, P., et al., *Plant Mol Biol* (1985) 5:149–154) surrounding a mutated form of acetolactate synthase from tobacco (surB, Lee, K., et al., *EMBO J* (1988) 7:1241–1248), cloning sites and the lacZalpha gene fragment. The resulting binary vector pBH1001 contains the chimeric e35S-Sfp-nos3' gene, and retains a single BamHI site for further DNA fragment insertion.

An 11.2 kbp NdeI/AvrII fragment containing the entire coding sequence of the DEBS1+TE (the eryAI coding sequenced fused with the coding sequence for the DEBS thioesterase (Kao, C.M., et al., (1995), supra) was isolated from pKOS018-97. This fragment was ligated with a 4.2 kbp NdeI/XbaI fragment containing a pUC replicon, ampicillin resistance gene, an e35S promoter and Cab22L leader ending at the NdeI site and an octopine synthase 3' fragment (DeGreve, H., et al., *J Mol Appl Genet* (1983) 1:499–511) beginning at the XbaI site. The resulting plasmid pBH1006 contains a chimeric e35S-DEBS1+TE-ocs3' gene.

A 12.6 kbp BamHI/BglII fragment containing the chimeric e35S-DEBS1+TE-ocs3' gene was isolated from pBH1006. This fragment was inserted into the BamHI site of pBH1001, which already contains a chimeric e35S-Sfp-nos3' gene between the T-DNA borders. The resulting binary vector pBH1008 contains both the e35S-Sfp-nos3' and e35S-DEBS1+TE-ocs3' chimeric genes.

A 14.2 kbp NdeI (blunt-ended)/BglII fragment containing a pUC replicon and ampicillin resistance gene ending at the BglII site and the DEBS1+TE coding sequence linked to the ocs3' end starting at the NdeI site, was isolated from pBH1006. This fragment was ligated to a 1 kbp SphI (blunt-ended)/BglII fragment containing the e35S-Cab22L leader-chloroplast transit peptide (ctp) sequence isolated from pER5526. The resulting plasmid pBH1009 contains a chimeric e35S-ctp-DEBS1+TE-ocs3' gene.

A 12.9 kbp BamHI/BglII fragment containing the e35S-ctp-DEBS1+TE-ocs3' chimeric gene was isolated from pBH1009. This fragment was inserted into the BamHI site of pAR4741. The resulting binary vector pBH1011 contains the chimeric e35S-ctp-DEBS1+TE-ocs3' gene, and retains a BamHI site for further fragment insertion.

A 3.9 kbp NcoI (blunt-ended)/BglII fragment containing the pUC replicon and ampicillin resistance gene and the Sfp coding sequence linked to the nos3' end starting at the NcoI site was isolated from pBH1000. This fragment was ligated to a 1 kbp SphI (blunt-ended)/BglII fragment containing the e35S-Cab22L leader-ctp sequence isolated from pER5526. The resulting plasmid pBH1010 contains a chimeric e35S-ctp-Sfp-nos3' gene.

A 2.0 kbp BamHI/BglII fragment containing the chimeric e35S-ctp-Sfp-nos3' gene was isolated from plasmid pBH1010. This fragment was inserted into the BamHI site of pAR4741. The resulting binary vector pSG5578 contains the chimeric e35S-ctp-Sfp-nos3' gene, and retains a BamHI site for further fragment insertion.

A 2.0 kbp BamHI/BglII fragment containing the chimeric e35S-ctp-Sfp-nos3' gene is isolated from plasmid pBH1010. This fragment is inserted into the BamHI site of pBH1011. The resulting binary vector pBH1012 contains the e35S-ctp-DEBS1+TE-ocs3' and the e35S-ctp-Sfp-nos3' chimeric genes, and retains a BamHI site for further fragment insertion.

A 5.5 kbp NdeI/XbaI fragment containing the MSAS coding sequence from *Penicillium patulum* was isolated from pKOS12-71d. This fragment was ligated to an NdeI/XbaI fragment containing the pUC replicon and ampicillin resistance gene, the e35S-cab22L leader ending at the NdeI site and the ocs3' end beginning at the XbaI site. The resulting plasmid pSG5540 contains a chimeric e35S-MSAS-ocs3' gene.

A 6 kbp NdeI/XbaI fragment containing a sequence that encodes a fusion protein of the MSAS protein from *Penicillium patulum* and the Sfp protein from *Bacillus subtilis* is isolated from pKOS14–69. This fragment is ligated to an NdeI/XbaI fragment containing the pUC replicon and ampicillin resistance gene, the e35S-cab22L leader ending at the NdeI site and the ocs3' end beginning at the XbaI site. The resulting plasmid pSG5541 contains a chimeric e35S-MSASSfp-ocs3' gene.

The e35S-MSAS-ocs3' chimeric gene was inserted into binary vector pWTT2144, between the HindIII and KpnI sites. Two separate fragments were isolated from pSG5540; one was a 5.1 kbp HindIII/AatII fragment and the other was a 1.95 kbp AatII/KpnI fragment. These fragments were ligated with the HindIII/KpnI digested pWTT2144. The resulting binary vector pSG5574 contains a chimeric e35S-MSAS-ocs3' gene.

The e35S-MSASSfp-ocs3' chimeric gene is inserted into binary vector pWTT2144, between the HindIII and KpnI sites. Two separate fragments are isolated from pSG554 1; one is a 5.1 kbp HindIII/AatII fragment, and the other is a 2.5 kbp AatII/KpnI fragment. These fragments are ligated with the HindIII/KpnI digested pWTT2144. The resulting binary vector pSG5575 contains a chimeric e35S-MSASSfp-ocs3' gene.

A 5.5 kbp NdeI (blunt-ended)/XbaI fragment containing the MSAS coding sequence was isolated from plasmid pSG5540. This was ligated to an SphI (blunt-ended)/XbaI fragment containing the pUC replicon and ampicillin resistance gene, the e35S-cab22L leader-ctp sequence ending at the SphI site and an ocs3' end beginning at the XbaI site. The resulting plasmid pSG5581 contains a chimeric e35S-ctp-MSAS-ocs3' gene.

A 6.0 kbp NdeI (blunt-ended)/XbaI fragment containing the MSASSfp coding sequence is isolated from plasmid pSG5541. This is ligated to an SphI (blunt-ended)/XbaI fragment containing the pUC replicon and ampicillin resistance gene, the e35S-cab22L leader-ctp sequence ending at the SphI site and an ocs3' end beginning at the XbaI site. The resulting expression vector pSG5582 contains a chimeric e35S-ctp-MSASSfp-ocs3' gene.

The e35S-ctp-MSAS-ocs3' chimeric gene was inserted into binary vector pWTT2144, between the HindIII and KpnI sites. Two separate fragments were isolated from pSG5581; one was a 5.1 kbp HindIII/AatII fragment and the other was a 1.90 kbp AatII/KpnI fragment. These fragments were ligated with the HindIII/KpnI digested pWTT2144. The resulting binary vector pSG5583 contains a chimeric e35S-ctp-MSAS-ocs3' gene.

The e35S-ctp-MSASSfp-ocs3' chimeric gene is inserted into binary vector pWTT2144, between the HindIII and KpnI sites. Two separate fragments are isolated from pSG5582; one is a 5.1 kbp HindIII/AatII fragment, and the other is a 2.5 kbp AatII/KpnI fragment. These fragments are ligated with the HindIII/KpnI digested pWTT2144. The resulting binary vector pSG5584 contains a chimeric e35S-ctp-MSASSfp-ocs3' gene.

EXAMPLE 6

Transformation of Tobacco Suspension Cultures
Establishment of Cultures:

Sterile tobacco plants (variety Petite Havana) were grown as shoot tip cultures on hormone-free Murashige and Skoog (MS) medium. Leaf disks were taken from these plants and inoculated onto agar-solidified MS media (1% agar) supplemented with 2 mg/l indolacetic acid (IAA) and 0.5 mg/l Benzylaminopurine (BA). Petri dishes with the leaf disks were incubated at 28° C. under lights with a 16 hour photoperiod for 3 weeks during which time undifferentiated cells (callus) formed on the cut edges. The callus was removed from the disks and transferred to liquid MS media with 0.2 mg/l 2,4-D as the only phytohormone.

These cell suspension cultures were incubated in the same conditions as the leaf disks but with shaking at 130 RPM. In these conditions the cultures grew as single cells and small cell clusters (mostly consisting of less than 100 cells) with a doubling time of about 2 days and were transferred weekly by adding about 2 ml settled cell volume (SCV) of cells to 50 ml of the liquid medium. The cultures could also be grown with 2 mg/l IAA and 0.5 mg/l BA, however under these conditions the suspensions grew much more slowly and consisted mostly of large cell aggregates.

Transformation of Suspension Cultures:

Suspension cultures are an ideal system for feeding chemical precursors and understanding how enzymes transform the precursors in plant cells.

The suspensions were transformed by cocultivation with an *Agrobacterium tumefaciens* strain carrying a binary plasmid which comprises the expression system gene for a PKS, e.g., the gene encoding the DEBS1-thioesterase, preferably along with an expression system for holo-ACP synthase, and also a selectable marker gene such as the ALS gene which provides resistance to the herbicide chlorsulfuron.

Transformation was done by mixing the Agrobacterium cells with the suspension cells in liquid medium. Cocultivation and selection is done in liquid medium by continuing to shake the Agrobacterium/tobacco cell mixture as before, but at 24° C. in darkness, or on solid medium by collecting the mixture on filter paper and transferring the filter paper with the cocultivating tobacco cells to solid media of the same composition as was used for the tobacco leaf disks. In either case, 100 μM Acetosyringone was added to the cocultivation media.

Selection for the transformed cells and counterselection to purge the cultures of the Agrobacteria is done by adding 50 μg/l chlorsulfuron and 500 mg/l carbenicillin to the same formulation of liquid or solid media as was used for cocultivation. In the case of the liquid transformation, the majority of the bacteria are rinsed away with fresh media prior to resuspension in the herbicide and antibiotic-containing media. In the case of solid transformations, the transformed callus is transferred into liquid media with or without selection and counterselection to re-establish suspension cultures.

Transformed (herbicide-resistant) cell suspensions containing the gene of interest were ready for analysis and/or feeding studies following 4–5 weeks of selection and counterselection. It is assumed that the transformed suspensions consist of a mixture of transformation events in which the T-DNA has integrated at multiple different random loci. These transformed suspensions can be used to produce polyketides.

Using the above procedure, plant cells modified to contain the expression system of pBH1008 of Example 5 were obtained. pBH1008 contains separate expression systems for DEBS1+TE and for Sfp, each under control of the 35S promoter.

Similarly, using the same procedure, but substituting for pBH1008, pBH1012, plant cells are transformed so as to comprise expression systems for DEBS1+TE and Sfp targeted to the chloroplast.

EXAMPLE 7

Transformation Protocol to Introduce Polyketide Synthase Genes into Tobacco

The source of leaf explants was in vitro grown tobacco plants (cv Petite Havana) cultured on TCMA medium (½ MS salts, B5 vitamins, 100 mg/l m-inositol, 600 mg/l MES, 20 g/l sucrose, pH 5.6 and solidified with 7 g/l TC agar) at 27° C. in 16 hr light. After removing the midrib from leaves they were cut into explants ca. 2×2 mm. Explants were floated on minAsuc medium containing an overnight culture of LBA4404 cells diluted to $5 \times 10^7$ cells/ml and containing the appropriate binary vector. After several minutes explants were transferred to plates containing TCMA basal medium supplemented with the following; 0.5 mg/l BAP, 2 mg/l IAA and 100 μM acetosyringone. Explants were cocultivated on this medium, overlayed with filter paper discs, at 24° C./dark for two days. Explants were then transferred to TCMA basal medium supplemented with the following; 0.5 mg/l BAP, 2 mg/l IAA, 25 μg/l chlorsulfuron (or 25 mg/l geneticin) and 250 mg/l carbenecillin. The explants were cultured under the same conditions as the in vitro shoots and after 3 weeks transgenic shoots had formed on most of the explants.

Using the above procedure, plants modified to contain the expression systems of pSG5574, pSG5575, and pBH1008 of Example 5 were obtained. pSG5574 contains an expression system for MSAS under control of the 35S promoter. pSG5575 contains an expression system for fusion protein between MSAS and Sfp under control of the 35S promoter.

Using the same procedure, but substituting for the above-named plasmids, pSG5584, which contains an expression system for the MSAS-Sfp fusion under control of the 35S promoter along with a ctp sequence, plants whereby the fusion protein is directed to the chloroplast are obtained. Similarly, cotransformation with pSG5578 (containing an expression system for Sfp) and pSG5583 (containing an expression system for MSAS) provides plants containing these proteins in the chloroplasts, thus permitting production of polyketides.

---

What is claimed is:

1. Plant cells, plant parts or plants modified to contain at least one expression system effective to produce an aromatic polyketide synthase (PKS), wherein said aromatic PKS comprises a ketosynthase/acyl transferase (KS/AT) catalytic region, a chain-length factor (CLF) catalytic region and an acyl carrier protein (ACP) activity and produces an aromatic polyketide in said plant cells, plant parts or plants.

2. The plant cells, plant parts or plants of claim 1 which have further been modified to contain at least one expression system effective to produce a holo-ACP synthase.

3. The plant cells, plant parts or plants of claim 2 wherein the expression system for PKS and the expression system for holo-ACP synthase are on separate vectors.

4. The plant cells, plant parts or plants of claim 2 wherein the expression system for PKS and the expression system for holo-ACP synthase are on the same vector.

5. The plant cells, plant parts or plants of claim 2 wherein the expression system for PKS and the expression system for holo-ACP synthase comprise an expression system for a fusion protein comprising said PKS and said holo-ACP synthase.

6. The plant cells, plant parts or plants of claim 1, wherein said KS/AT encoding nucleotide sequence, CLF encoding nucleotide sequence, and ACP encoding nucleotide sequence are derived from the same aromatic polyketide synthase (PKS).

7. The plant cells, plant parts or plants of claim 1 wherein at least one of said KS/AT encoding nucleotide sequence, CLF encoding nucleotide sequence, and ACP encoding nucleotide sequence is derived from a different aromatic polyketide synthase (PKS).

8. The plant cells, plant parts or plants of claim 1 which further contain an expression system for a cell-based detection system for a polyketide.

9. A plant cell, plant part or plant of claim 2 which further contains an expression system for a cell-based detection system for a polyketide.

10. Plant cells, plant parts or plants modified to contain at least one expression system effective to produce a fungal polyketide synthase (PKS), wherein said fungal PKS comprises a ketosynthase/acyl transferase (KS/AT) catalytic region and an acyl carrier protein (ACP) activity and produces a fungal polyketide in said plant cells, plant parts or plants.

11. The plant cells, plant parts or plants of claim 10 which have further been modified to contain at least one expression system effective to produce a holo-ACP synthase.

12. The plant cells, plant parts or plants of claim 11 wherein the expression system for PKS and the expression system for holo-ACP synthase are on separate vectors.

13. The plant cells, plant parts or plants of claim 11 wherein the expression system for PKS and the expression system for holo-ACP synthase are on the same vector.

14. The plant cells, plant parts or plants of claim 11 wherein the expression system for PKS and the expression system for holo-ACP synthase comprise an expression system for a fusion protein comprising said PKS and said holo-ACP synthase.

15. The plant cells, plant parts or plants of claim 10, wherein said KS/AT encoding nucleotide sequence, and ACP encoding nucleotide sequence are derived from the same fungal polyketide synthase.

16. The plant cells, plant parts or plants of claim 10 wherein the KS/AT encoding nucleotide sequence, and the ACP encoding nucleotide sequence are derived from different fungal polyketide synthases.

17. The plant cells, plant parts or plants of claim 10 which further contain an expression system for a cell-based detection system for a polyketide.

18. A plant cell, plant part or plant of claim 11 which further contains an expression system for a cell-based detection system for a polyketide.

19. A method to produce a functional polyketide synthase which method comprises culturing the plant cells, plant parts or plants of claim 2 under conditions wherein said functional PKS is produced.

20. A method to produce a functional polyketide synthase which method comprises culturing the plant cells, plant parts or plants of claim 11 under conditions wherein said functional PKS is produced.

21. The plant cells, plant parts or plants of claim 1 wherein said at least one expression system further comprises means for targeting the PKS protein produced to a cellular compartment.

22. The plant cells, plant parts or plants or claim 21, wherein the cellular compartment is a plastid.

23. The plant cells, plant parts or plants of claim 21, wherein said means comprises a transit peptide sequence coupled to the N-terminus of the protein to be targeted.

24. The plant cells, plant parts or plants of claim 1, wherein the nucleotide sequence encoding said PKS has been modified to utilize codons preferred in plants; and/or
to eliminate cryptic splice sites; and/or
to alter GC/AT content.

25. The plant cells, plant parts or plants of claim 10 wherein said at least one expression system further comprises means for targeting the PKS protein produced to a cellular compartment.

26. The plant cells, plant parts or plants of claim 25, wherein the cellular compartment is a plastid.

27. The plant cells, plant parts or plants of claim 25, wherein said means comprises a transit peptide sequence coupled to the N-terminus of the protein to be targeted.

28. The plant cells, plant parts or plants of claim 10, wherein the nucleotide sequence encoding said PKS has been modified to utilize codons preferred in plants; and/or
to eliminate cryptic splice sites; and/or
to alter GC/AT content.

29. A method to produce a functional polyketide synthase which method comprises culturing the plant cells, plant parts or plants of claim 21 under conditions where said functional PKS is produced.

30. A method to produce a functional polyketide synthase which method comprises culturing the plant cells, plant parts or plants of claim 24 under conditions where said functional PKS is produced.

31. A method to produce a functional polyketide synthase which method comprises culturing the plant cells, plant parts or plants of claim 25 under conditions where said functional PKS is produced.

32. A method to produce a functional polyketide synthase which method comprises culturing the plant cells, plant parts or plants of claim 28 under conditions where said functional PKS is produced.

33. The plant cells, plant parts or plants of claim 10 wherein said fungal PKS is 6-MSAS.

34. The plant cells, plant parts or plants of claim 11 wherein said fungal PKS is 6-MSAS.

35. The plant cells, plant parts or plants of claim 12 wherein said fungal PKS is 6-MSAS.

36. The plant cells, plant parts or plants of claim 13 wherein said fungal PKS is 6-MSAS.

37. The plant cells, plant parts or plants of claim 14 wherein said fungal PKS is 6-MSAS.

38. The plant cells, plant parts or plants of claim 15 wherein said fungal PKS is 6-MSAS.

39. The plant cells, plant parts or plants of claim 16 wherein said fungal PKS is 6-MSAS.

40. The plant cells, plant parts or plants of claim 17 wherein said fungal PKS is 6-MSAS.

41. The plant cells, plant parts or plants of claim 18 wherein said fungal PKS is 6-MSAS.

42. The plant cells, plant parts or plants of claim 20 wherein said fungal PKS is 6-MSAS.

43. The plant cells, plant parts or plants of claim 25 wherein said fungal PKS is 6-MSAS.

44. The plant cells, plant parts or plants of claim 26 wherein said fungal PKS is 6-MSAS.

45. The plant cells, plant parts or plants of claim 27 wherein said fungal PKS is 6-MSAS.

46. The plant cells, plant parts or plants of claim 28 wherein said fungal PKS is 6-MSAS.

47. The method of claim 31 wherein said fungal PKS is 6-MSAS.

48. The method of claim 28 wherein said fungal PKS is 6-MSAS.

49. The plant cells, plant parts or plants of claim 10 which are tobacco plant cells, tobacco plant parts or tobacco plants.

50. The plant cells, plant parts or plants of claim 11 which are tobacco plant cells, tobacco plant parts or tobacco plants.

51. The plant cells, plant parts or plants of claim 14 which are tobacco plant cells, tobacco plant parts or tobacco plants.

52. The method of claim 25 which are tobacco plant cells, tobacco plant parts or tobacco plants.

53. The method of claim 28 which are tobacco plant cells, tobacco plant parts or tobacco plants.

54. The plant cells, plant parts or plants of claim 33 which are tobacco plant cells, tobacco plant parts or tobacco plants.

55. The plant cells, plant parts or plants of claim 34 which are tobacco plant cells, tobacco plant parts or tobacco plants.

56. The plant cells, plant parts or plants of claim 37 which are tobacco plant cells, tobacco plant parts or tobacco plants.

57. The plant cells, plant parts or plants of claim 43 which are tobacco plant cells, tobacco plant parts or tobacco plants.

58. The plant cells, plant parts or plants of claim 28 which are tobacco plant cells, tobacco plant parts or tobacco plants.

59. The method of claim 47 which are tobacco plant cells, tobacco plant parts or tobacco plants.

60. The method of claim 48 which are tobacco plant cells, tobacco plant parts or tobacco plants.

61. The plant cells, plant parts or plants of claim 1 which are tobacco plant cells, tobacco plant parts or tobacco plants.

62. The plant cells, plant parts or plants of claim 2 which are tobacco plant cells, tobacco plant parts or tobacco plants.

63. The plant cells, plant parts or plants of claim 5 which are tobacco plant cells, tobacco plant parts or tobacco plants.

64. The method of claim 29 which are tobacco plant cells, tobacco plant parts or tobacco plants.

65. The method of claim 30 which are tobacco plant cells, tobacco plant parts or tobacco plants.

* * * * *

UNITED STATES PATENT AND TRADEMARK OFFICE
CERTIFICATE OF CORRECTION

PATENT NO.    : 6,262,340 B1                                                Page 1 of 1
DATED         : July 17, 2001
INVENTOR(S)   : Mary Betlach et al.

It is certified that error appears in the above-identified patent and that said Letters Patent is hereby corrected as shown below:

Column 26,
Line 58, replace Claim 42 with:
    42.    The method of Claim 20, wherein the functional PKS produced by the cultured plant cells, plant parts, or plants is 6-MSAS.

Column 27,
Line 3, replace Claim 48 with:
    48.    The plant cells, plant parts, or plants of Claim 28 wherein the PKS is 6-MSAS.
Line 11, replace Claim 52 with:
    52.    The plant cells, plant parts, or plants of Claim 25 which are tabacco cells, tobacco parts, or tobacco plants.
Line 13, replace Claim 53 with:
    53.    The plant cells, plant parts, or plants of Claim 28 which are tobacco cells, tobacco parts, or tobacco plants.

Signed and Sealed this

Eleventh Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,262,340 B1
DATED         : July 17, 2001
INVENTOR(S)   : Mary Betlach et al.

It is certified that error appears in the above-identified patent and that said Letters Patent is hereby corrected as shown below:

Drawings,
Replacement Formal Drawings for U.S. Patent No. 6,262,340

Signed and Sealed this

Tenth Day of May, 2005

JON W. DUDAS
*Director of the United States Patent and Trademark Office*